US011179109B1

(12) United States Patent
Katra et al.

(10) Patent No.: US 11,179,109 B1
(45) Date of Patent: *Nov. 23, 2021

(54) APPARATUS AND METHOD FOR CARDIAC SIGNAL NOISE DETECTION AND DISPOSITION BASED ON PHYSIOLOGIC RELEVANCE

(71) Applicant: Greatbatch Ltd., Clarence, NY (US)

(72) Inventors: Rodolphe Katra, Blaine, MN (US); Tyler Stigen, Champlin, MN (US); Niranjan Chakravarthy, Eden Prairie, MN (US)

(73) Assignee: Greatbatch Ltd., Clarence, NY (US)

( * ) Notice: Subject to any disclaimer, the term of this patent is extended or adjusted under 35 U.S.C. 154(b) by 292 days.

This patent is subject to a terminal disclaimer.

(21) Appl. No.: 16/170,550

(22) Filed: Oct. 25, 2018

Related U.S. Application Data

(63) Continuation of application No. 14/832,311, filed on Aug. 21, 2015, now Pat. No. 10,123,745.

(51) Int. Cl.
*A61B 5/316* (2021.01)
*A61B 5/00* (2006.01)
*A61B 5/318* (2021.01)

(52) U.S. Cl.
CPC ............ *A61B 5/7207* (2013.01); *A61B 5/316* (2021.01); *A61B 5/318* (2021.01)

(58) Field of Classification Search
CPC .. A61N 1/3704; A61N 1/3718; A61B 5/7207; A61B 5/04017; A61B 5/0428; A61B 5/318; A61B 5/316
See application file for complete search history.

(56) References Cited

U.S. PATENT DOCUMENTS

| | | | |
|---|---|---|---|
| 5,522,857 | A | 6/1996 | Van Krieken |
| 5,861,008 | A | 1/1999 | Obel et al. |
| 6,358,201 | B1 | 3/2002 | Childre et al. |
| 6,836,680 | B2 | 12/2004 | Kuo |
| 7,111,468 | B2 | 9/2006 | Choi et al. |
| 7,155,275 | B2 | 12/2006 | Linder et al. |
| 7,406,877 | B2 | 8/2008 | Maurin |
| 8,135,470 | B2 | 3/2012 | Keimel et al. |
| 8,140,143 | B2 | 3/2012 | Picard et al. |
| 8,265,737 | B2 | 9/2012 | Warren et al. |
| 8,317,717 | B2 | 11/2012 | Siejko et al. |
| 8,517,912 | B2 | 8/2013 | Clare |
| 8,529,457 | B2 | 9/2013 | Devot et al. |

(Continued)

FOREIGN PATENT DOCUMENTS

CN 103479429 1/2014

*Primary Examiner* — George R Evanisko
(74) *Attorney, Agent, or Firm* — Michael F. Scalise

(57) ABSTRACT

An apparatus comprises an input configured to receive electrocardiogram (ECG) data detected by a patient monitoring device, the ECG data containing a physiologic signal and one or more segments of noise within the ECG data. A scrubber comprises a plurality of scrubbing modules each configured to process the ECG data and noise in a manner differing from other scrubbing modules. The scrubber is configured to filter the one or more noise segments that overlap with the physiologic signal, and consolidate the ECG data to eliminate the one or more noise segments that are non-overlapping with the physiologic signal. An output is configured to output scrubbed ECG data.

20 Claims, 17 Drawing Sheets

(56) References Cited

U.S. PATENT DOCUMENTS

| | | |
|---|---|---|
| 8,639,316 B2 | 1/2014 | Sarkar |
| 8,666,482 B2 | 3/2014 | Wegerif |
| 8,744,556 B2 | 6/2014 | Mahajan et al. |
| 8,775,120 B2 | 7/2014 | Molettiere et al. |
| 8,831,727 B2 | 9/2014 | Stalsberg et al. |
| 10,123,745 B1 * | 11/2018 | Katra .................. A61B 5/0402 |
| 2009/0259271 A1 * | 10/2009 | Allavatam ........... A61N 1/3987 607/25 |
| 2013/0245478 A1 | 9/2013 | Zhang |

* cited by examiner

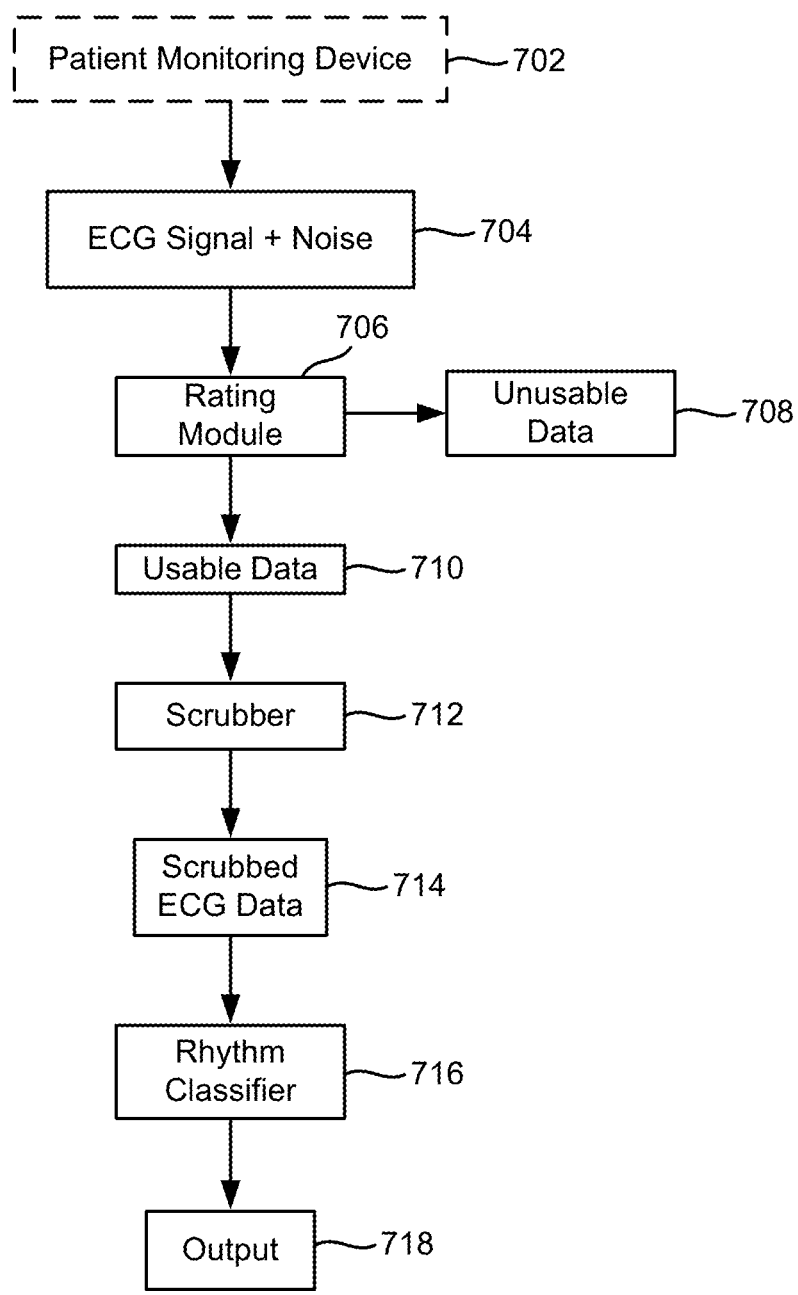

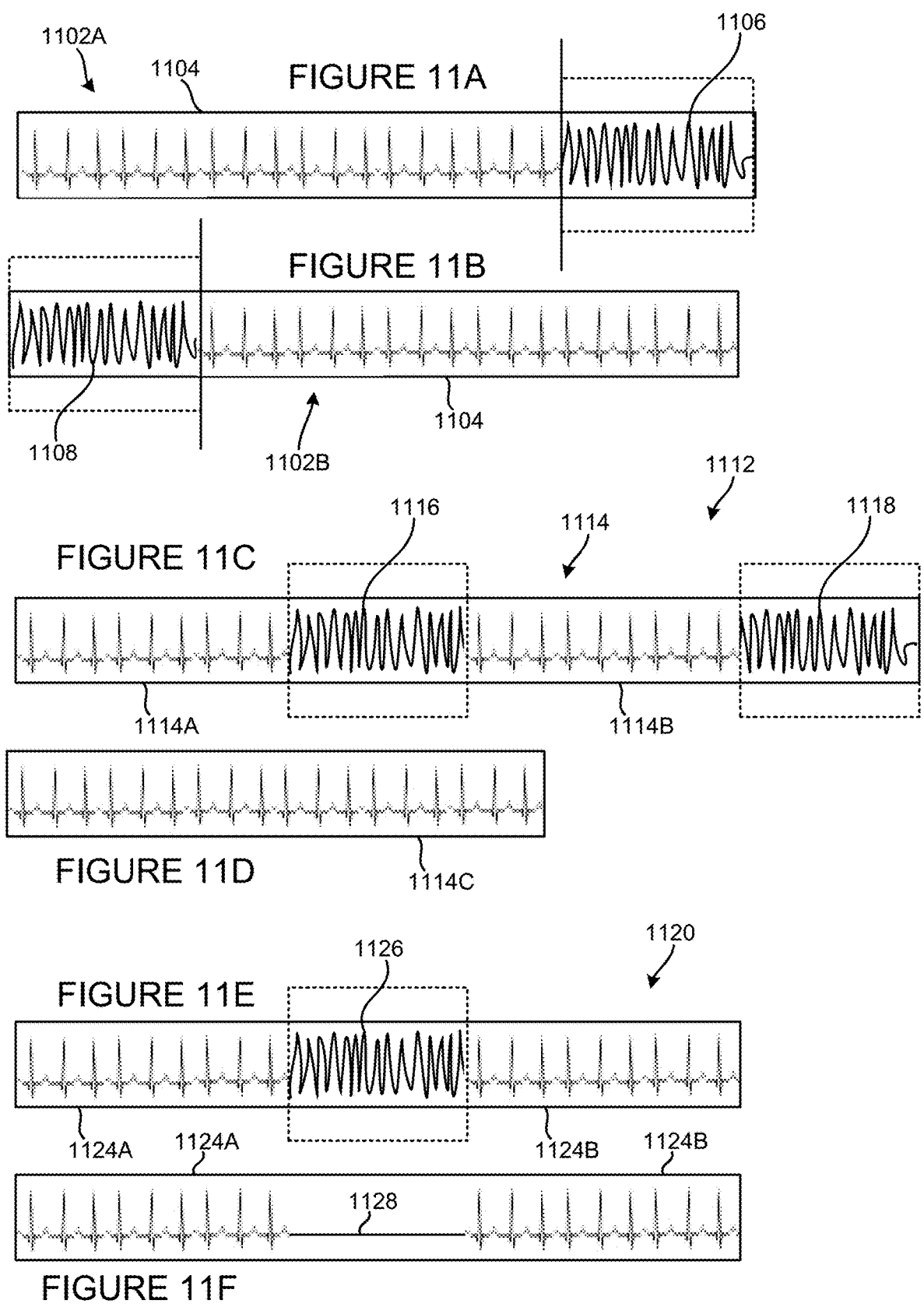

APPARATUS AND METHOD FOR CARDIAC SIGNAL NOISE DETECTION AND DISPOSITION BASED ON PHYSIOLOGIC RELEVANCE

RELATED APPLICATIONS

This application is a continuation of U.S. patent application Ser. No. 14/832,311, filed on Aug. 21, 2015, now U.S. Pat. No. 10,123,745, which is incorporated herein by reference in its entirety.

TECHNICAL FIELD

This patent document pertains generally to noise detection and more particularly, but not by way of limitation, to noise detection in a cardiac signal.

BACKGROUND

Noise in signals can be problematic. This can be especially true with cardiac signals. In some instances, noise sources can cause false triggers of arrhythmia recording devices leading to high false positive rates. In some instances, one or more noise sources in a cardiac recording can conceal or completely eliminate a relevant cardiac signal. Recording excessive amounts of noise in addition to cardiac signal content can be wasteful, in terms of processing time, memory usage, and time required to evaluate cardiac signal information (e.g., electrocardiogram data or strips) by a clinician.

SUMMARY

Embodiments of the disclosure are directed to a method comprising receiving electrocardiogram (ECG) data detected by a patient monitoring device, the ECG data containing a physiologic signal and sporadic noise. The method also comprises identifying a temporal occurrence of the ECG data and a temporal occurrence of one or more segments of noise within the ECG data. The method further comprises scrubbing the ECG data by filtering the one or more noise segments that overlap with the physiologic signal, and consolidating the ECG data to eliminate the one or more noise segments that are non-overlapping with the physiologic signal. The method also comprises generating an output comprising scrubbed ECG data.

Other embodiments are directed to an apparatus comprising an input configured to receive electrocardiogram (ECG) data detected by a patient monitoring device, the ECG data containing a physiologic signal and one or more segments of noise within the ECG data. A scrubber comprises a plurality of scrubbing modules each configured to process the ECG data and noise in a manner differing from other scrubbing modules. The scrubber is configured to filter the one or more noise segments that overlap with the physiologic signal, and consolidate the ECG data to eliminate the one or more noise segments that are non-overlapping with the physiologic signal. An output is configured to output scrubbed ECG data.

The above summary is not intended to describe each disclosed embodiment or every implementation of the present disclosure. The figures and the detailed description below more particularly exemplify illustrative embodiments

BRIEF DESCRIPTION OF THE DRAWINGS

Throughout the specification reference is made to the appended drawings, where like reference numerals designate like elements, and wherein:

FIG. 7 illustrates an embodiment of a physiologic signal processor which includes a rating module, a noise scrubber, and a rhythm classifier in accordance with various embodiments;

FIGS. 11A-11F illustrate different ECG data containing noise subject to consolidation by a noise scrubber in accordance with various embodiments;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

The present inventors have recognized, among other things, that noise in a cardiac signal is generally undesirable and have sought to lessen if not eliminate noise in a cardiac signal. The present inventors have recognized that it is desirable to provide an apparatus or method for cardiac signal noise detection and disposition based on physiologic relevance, through noise reduction in conjunction with characterization and tiered prioritization of data.

In the following detailed description, reference is made to the accompanying drawing which form a part hereof, and in which is shown by way of illustration specific examples in which the present description may be practiced. These examples are described in sufficient detail to enable those skilled in the art to practice the present subject matter, and it is to be understood that other examples may be utilized and that structural changes may be made without departing from the scope of the present description. Therefore, the following detailed description is not to be taken in a limiting sense.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, or process that includes elements in addition to those listed after such a term are still deemed to fall within the scope of the description. Moreover, the terms "first," "second," and "third," etc. are used merely as labels, and are not intended to impose numerical requirements on their objects.

Figure 1:
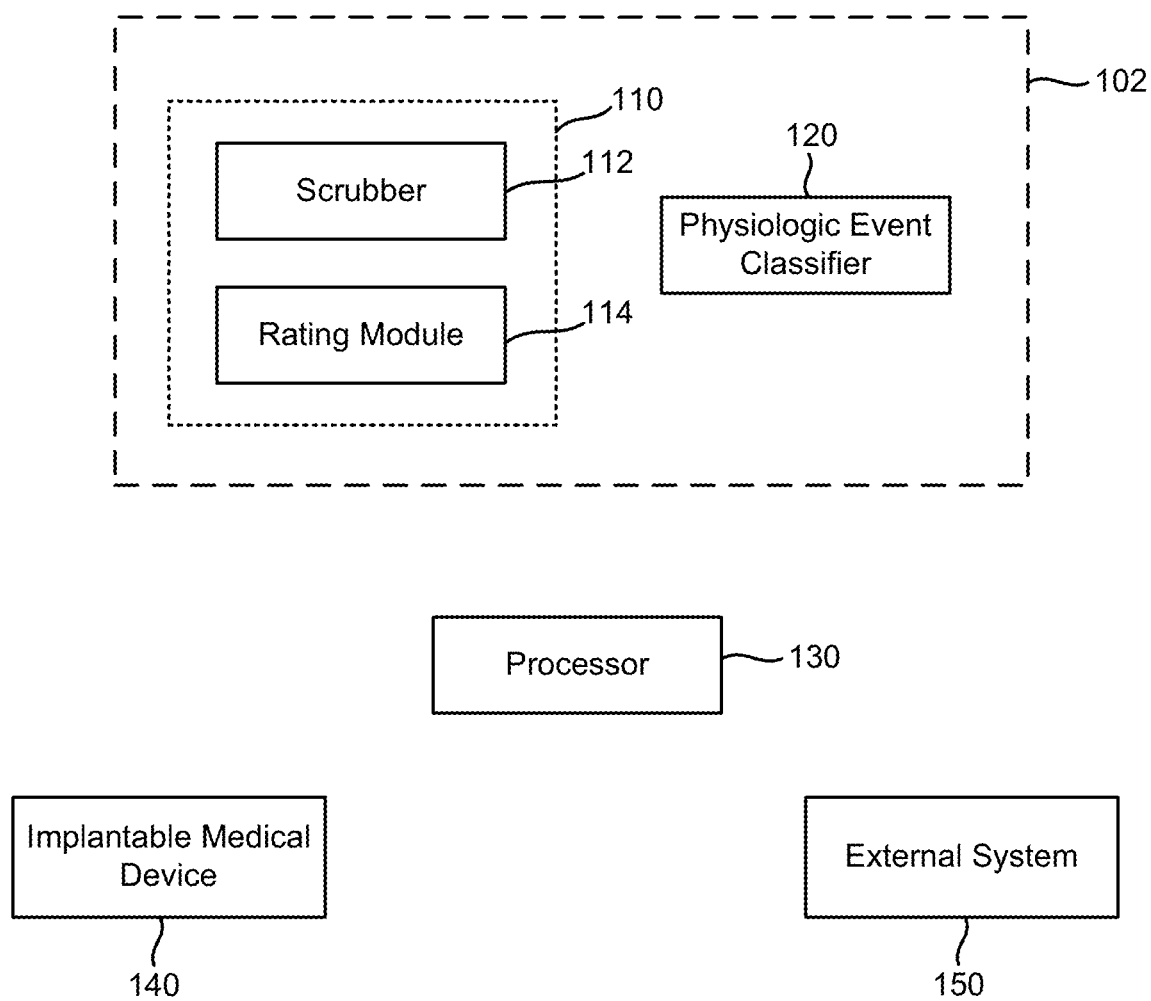
FIG. 1 is a block diagram of a system for processing physiologic signals and noise in accordance with various embodiments.

FIG. 1 is a block diagram of a system for processing physiologic signals and noise in accordance with various embodiments. The system shown in FIG. 1 includes a physiologic signal processor 102 configured to receive physiologic signal data containing a physiologic signal and one or more artifactual segments of noise confounding the physiologic signal. In various embodiments, the physiologic signal data received by the physiologic signal processor 102 is produced by a patient monitoring device, such as an implantable or external device that monitors a patient's electrocardiogram (ECG). For example, the ECG data received by the physiologic signal processor 102 can be equivalent in signal content to that which is presented on an ECG strip. Although embodiments disclosed herein are described as being implemented to process ECG data, it is understood that other forms of physiologic signal data are contemplated (e.g., electrogram (EGM), electroencephalogram (EEG), electromyogram (EMG)). The physiologic signal processor 102 includes a noise processor 110. In some embodiments, the physiologic signal processor 102 also includes a physiologic rate and/or rhythm classifier 120, it being understood that the classifier 120 may be excluded in various embodiments.

The term ECG signal or data is used throughout the disclosure and, in particular, in the context of noise that can obscure or mask the presence of ECG signal content that is clinically relevant (e.g., usable for diagnostic purposes). It is understood that the term ECG signal or data used herein generally refers to an ECG signal or data that contains clinically-relevant content. In some portions of the disclosure, the term clinically-relevant ECG signal or data is explicitly used, while in others this connotation of the term is implicit.

According to some embodiments, the noise processor 110 includes a noise scrubber 112. The scrubber 112 typically comprises a multiplicity of noise scrubbing modules each configured to process the physiologic signal and noise in a manner differing from other scrubbing modules. For example, the scrubber 112 includes one or more scrubbing modules that are designed to operate on noise segments that overlap with a physiologic event. The scrubber 112 also includes one or more scrubbing modules that are designed to operate on noise segments that are non-overlapping with a physiologic event. A scrubbed physiologic signal (e.g., a scrubbed ECG signal) is produced at the output of scrubber 112. The scrubber 112 may be the exclusive component of the noise processor 110 or, in accordance with various embodiments, may be combined with other components.

In other embodiments, the noise processor 110 includes a rating module 114, which may be the exclusive component of the noise processor 110 or, in some embodiments, may be combined to operate with the scrubber 112. The rating module 114 is configured to rate the physiologic signal data input to the noise processor 110 based on the presence or absence of both the physiologic signal and noise, as well as input from other sources external to the rating module 114, such as patient activated markers. The rating module 114 analyzes the physiologic signal data for noise content that would render the physiologic signal either undetectable or unusable. The rating module 114 employs a decision matrix to distinguish physiologic signal data that can be readily processed from physiologic signal data that requires scrubbing or further processing. The rating module 114 can be configured to flag or annotate the physiologic signal data, such as by adding noise markers to the data. The rating module 114 can facilitate the production of a multiplicity of data streams that differ in terms of noise content. The different data streams can be processed in a manner appropriate for each data stream in accordance with various embodiments.

According to further embodiments, the physiologic signal processor 102 includes a physiologic event classifier 120. In general terms, the physiologic event classifier 120 is configured to detect and classify physiologic events based on pre-specified criteria within the physiologic signal data. In various embodiments disclosed herein, the physiologic event classifier 120 is implemented as a general rhythm classifier. In various embodiments disclosed herein, the physiologic event classifier 120 is implemented solely as a rate classifier. In some embodiments, the physiologic event classifier 120 is implemented to operate in cooperation with the scrubber 112. In other embodiments, the physiologic event classifier 120 is implemented to operate cooperatively with both the scrubber 112 and the rating module 114.

A physiologic event classifier 120 implemented as a rhythm classifier, according to various embodiments, is configured to classify a cardiac rhythm based on ECG data received by the physiologic signal processor 102. In some embodiments, the rhythm classifier implements a known rate classification algorithm for classifying cardiac rhythms, such as bradycardia, tachycardia, and asystole. In other embodiments, the rhythm classifier uses algorithms that analyze the morphology of ECG signals for classifying cardiac rhythms. Various known template matching and processing algorithms can be employed for analyzing the morphology of ECG signals for purposes of classifying cardiac rhythms. Other algorithms can be implemented by the rhythm classifier when classifying cardiac rhythms, such as pattern-based and wavelet-based algorithms.

The system shown in FIG. 1 can include a processor 130 which can be configured to coordinate the operations of the physiologic signal processor 102 and the flow of data through the physiologic signal processor 102 and other system components. In some embodiments, some or all of the components of the physiologic signal processor 102 can be implemented in an implantable medical device 140, such as a loop recorder or a cardiac rhythm management device.

In other embodiments, some or all of the components of the physiologic signal processor 102 can be implemented in an external system 150, such as a system that includes a desktop or laptop computer. For example, a patient monitoring device (e.g., implantable or external) can be implemented to monitor and store ECG data. The ECG data can be communicated in batch mode or in real-time to an external system 150 which includes one or more of the components of the physiologic signal processor 102. The received ECG data can be processed by the external system 150 according to the embodiments described herein.

Figure 2:
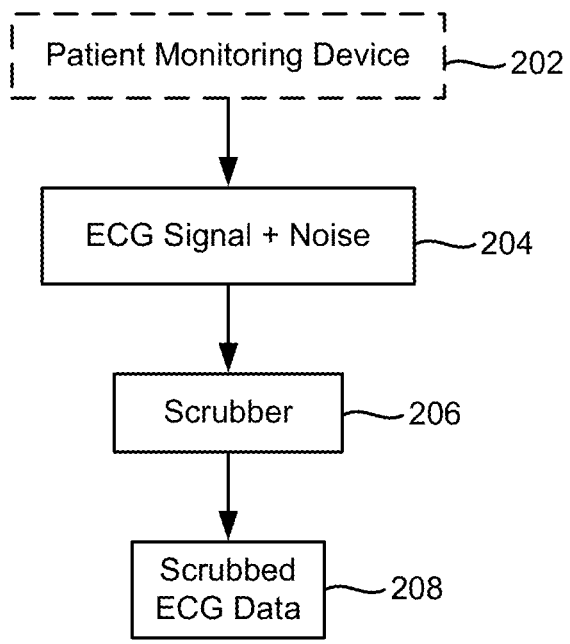
FIG. 2 illustrates an embodiment of a physiologic signal processor configured to receive ECG data from a patient monitoring device in accordance with various embodiments.

FIGS. 2 through 15 illustrate various embodiments or aspects of a physiologic signal processor that incorporates one or a combination of the components shown in FIG. 1. FIG. 2 illustrates an embodiment of a physiologic signal processor configured to receive ECG data from a patient monitoring device 202. The ECG data 204 contains an ECG signal and one or more segments of noise. A scrubber 206 is configured to operate on the ECG data in a manner discussed herein. Scrubbed ECG data is produced at an output 208 of the scrubber 206.

Figure 3:
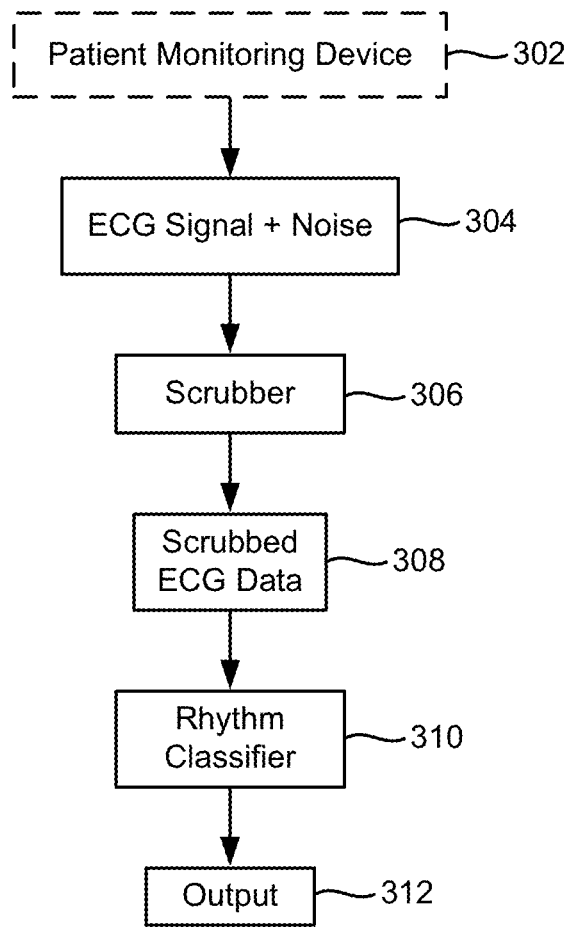
FIG. 3 illustrates an embodiment of a physiologic signal processor configured to receive ECG data from a patient monitoring device in accordance with various embodiments.

FIG. 3 illustrates an embodiment of a physiologic signal processor configured to receive ECG data 304 from a patient monitoring device 302. The ECG data 304, which includes an ECG signal and noise, is input to a scrubber 306 which produces scrubbed ECG data 308 at its output. The scrubbed ECG data 308 is input to a rhythm classifier 310, which is configured to classify cardiac rhythms based on the scrubbed ECG data 308. Either the scrubber 306 or the rhythm classifier 310 is configured to determine if a sufficient amount of ECG signal content is present in the scrubbed ECG data 308 to properly classify cardiac rhythms. Data produced by the rhythm classifier 310 is provided at an output 312. For example, data output from the rhythm classifier 310 may include an indication of normal sinus rhythm, bradycardia, tachycardia, and asystole, for example. The data output by the rhythm classifier 310 or the scrubber 306 may also include various cardiac event markers and/or noise markers that can be used to annotate ECG data provided at the output 312.

In general, the duration and number of ECG data recordings produced by the patient monitoring device 302 can vary. In some cases, the ECG data produced by the patient monitoring device 302 resulted as a response to a patient-initiated command issued to the patient monitoring device 302. For example, a patient may be able to initiate recording of cardiac activity for a period of 7 minutes by actuating a control on an external medical device or on an external communication device that interfaces with an implantable medical device (e.g., a loop recorder). In some cases, device triggered recording of ECG data can result in ECG recordings of 1 minute in duration, based on preset criteria for triggering such as a minimum heart rate or a certain type of rhythm, for example. In other cases, a trending algorithm can be implemented by an external or implantable medical device, wherein 20 second ECG recordings are regularly obtained, based on a specific time lapse. In these scenarios involving different amounts of ECG data, the rhythm classifier 310 (or the scrubber 306) is configured to evaluate whether a sufficient amount of ECG data is available after scrubbing to allow for proper classification of various cardiac rhythms, it being understood that different cardiac rhythms may require a different minimum amount of ECG data to be accurately classified by the rhythm classifier 310.

Figure 4:
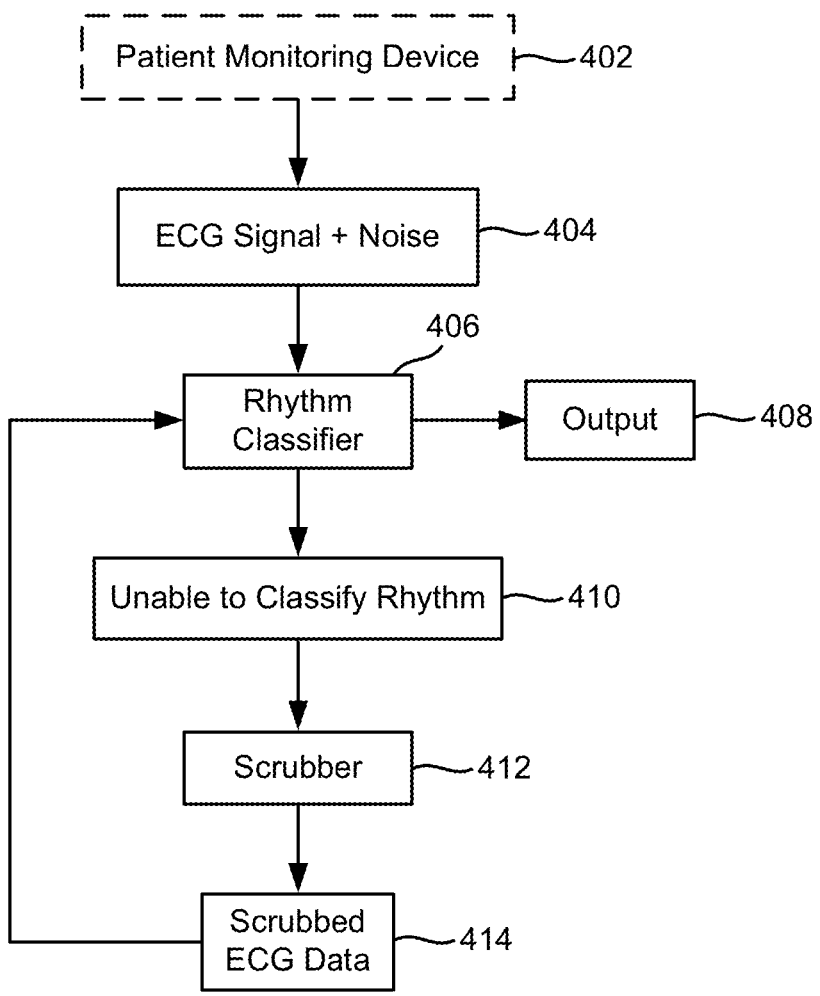
FIG. 4 illustrates an embodiment of a physiologic signal processor configured to receive ECG data from a patient monitoring device in accordance with various embodiments.

FIG. 4 illustrates an embodiment of a physiologic signal processor configured to receive ECG data 404 from a patient monitoring device 402. In this embodiment, ECG data 404 is initially communicated to a rhythm classifier 406. If the ECG data 404 is suitable for classification, the rhythm classifier 406 generates an output 408 indicating the classified cardiac rhythm. If the ECG data cannot be classified 410, such as due to the presence of noise, the ECG data is communicated to a scrubber 412. Scrubbed ECG data 414 is communicated back to the rhythm classifier 406 which, once again, attempts to classify the cardiac rhythm using the scrubbed ECG data 414. If the rhythm classifier 406 is unable to classify the rhythm after repeated attempts, the ECG data 414 is discarded and processing is terminated, with a specific annotation to the nature of the data classification failure provided at the output 408 to indicate such failure.

Figure 5:
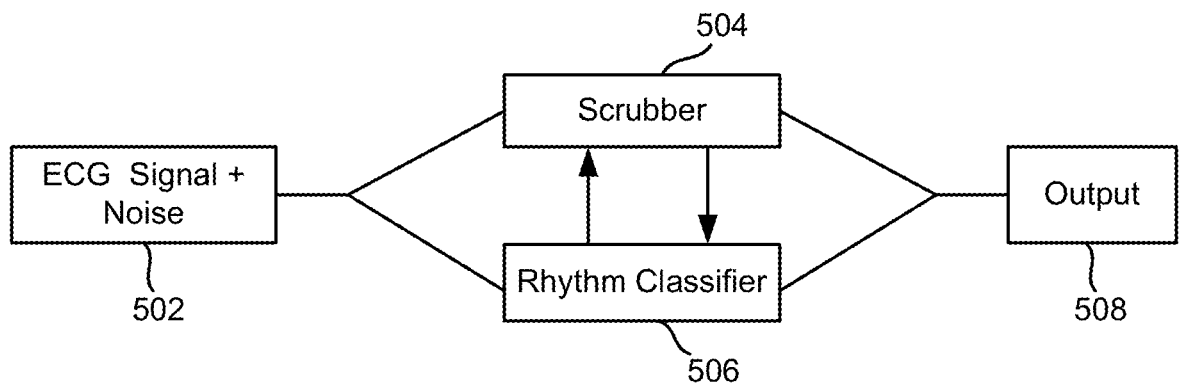
FIG. 5 illustrates an embodiment of a physiologic signal processor which involves parallel processing between a noise scrubber and a rhythm classifier in accordance with various embodiments.

FIG. 5 illustrates an embodiment of a physiologic signal processor which involves parallel processing between a scrubber 504 and a rhythm classifier 506. According to the embodiment shown in FIG. 5, ECG data 502 is received by the scrubber 504 and the rhythm classifier 506 concurrently, with different portions of the ECG data 502 being distributed to the two components 504 and 506. As such, each of the scrubber 504 and rhythm classifier 506 operates on different portions of ECG data 502 simultaneously.

The following is a description of ECG data processing that originates at the rhythm classifier 506. For ECG data portions that can be classified by the rhythm classifier 506, these portions are classified then communicated to the output 508, thereby bypassing the scrubber 504. For ECG data portions that cannot be classified by the rhythm classifier 506, these portions are communicated to the scrubber 504 for processing. After scrubbing the ECG data portions, the scrubber 504 communicates the scrubbed portions back to the rhythm classifier 506 for classification. Assuming the scrubbed portions are successfully classified, these portions are communicated to the output 508. If the scrubbed portions cannot be successfully classified, these portions of the ECG signal data are discarded or passed on so that they can be evaluated manually by a clinician.

The following is a description of ECG data processing that originates at the scrubber 504. For ECG data portions that do not need to be scrubbed, these portions are communicated to the rhythm classifier 506 for classification. For ECG data portions that require scrubbing, the scrubber 504 processes these portions. The scrubbed ECG data portions are then communicated back to the rhythm classifier 506 for classification. Assuming the scrubbed portions are successfully classified, these portions are communicated to the output 508. If the scrubbed portions cannot be successfully classified, these portions of the ECG data are discarded or passed on so that they can be evaluated manually by a clinician. In some embodiments, the scrubber 504 and the rhythm classifier 506 conduct parallel processing on data 502, such that the concurrently processed output of the scrubber 504 and the rhythm classifier 506 gates the output 508. If in the course of parallel processing, the scrubber 504 or the rhythm classifier 506 flag the physiologic signal 502 according to certain preset criteria, the parallel processing modality terminates and the flow of data processing switches to serial processing based on the nature of the flag, such as scrubber processing first followed by rhythm classification, or rhythm classification first followed by scrubbing, as proposed in previous embodiments outlined in FIG. 3 and FIG. 4. The data flow switching described herein, would be conducted in real-time as dictated by the nature of physiologic signal 502 being processed. The data flow would then revert back to parallel processing for the following incoming physiologic signal 502.

Figure 6:
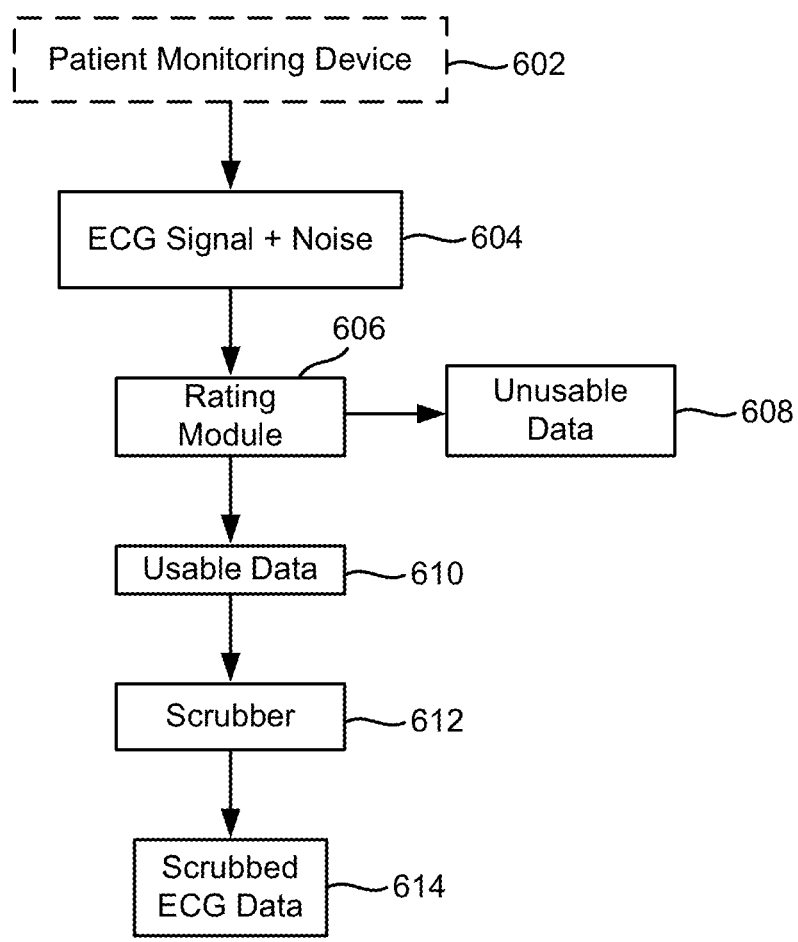
FIG. 6 illustrates an embodiment of a physiologic signal processor which includes a rating module in accordance with various embodiments.

FIG. 6 illustrates an embodiment of a physiologic signal processor which includes a rating module 606. The rating module 606 receives ECG data 604 produced by a patient monitoring device 602. As was discussed previously, the rating module 606 is configured to rate the ECG data based on the presence or absence of both an ECG signal and noise. In some cases, the rating module 606 determines that some of the ECG data is unusable 608. The unusable data 608 may be discarded or, in some embodiments, stored for later review by a clinician. ECG data 610 determined by the rating module 606 to be usable is communicated to a scrubber 612, which produces scrubbed ECG data 614. The rating module 606 can use preset thresholds for determining data usability. These thresholds could be static or adaptive over time, as well as utilizing parametric or non-parametric input, such as allowances for certain signal to noise levels, provided by the healthcare provider.

FIG. 7 illustrates an embodiment of a physiologic signal processor which includes a rating module 706, a scrubber 712, and a rhythm classifier 716. In the embodiment shown in FIG. 7, ECG data 704 is received from a patient monitoring device 702, and communicated to a rating module 706. The rating module 706 determines which ECG data 704 is usable 710 or unusable 708. The usable data 710 is communicated to a scrubber 714, which produces scrubbed ECG data 714. The scrubbed ECG data 714 is communicated to the rhythm classifier 716, which classifies the cardiac rhythm. The scrubbed ECG data along with classification data is communicated to an output 718. It is also anticipated that the order of data scrubbing and rhythm classification can be conducted in the reverse order where classification occurs first followed by data scrubbing, or using a parallel processing scheme as described previously.

Noise sources can cause false triggering of arrhythmia recording devices, potentially leading to high false positive rates. Conversely, noise can also cause missed detections of arrhythmias by masking the underlying triggers, leading to high false negative rates. In some examples, a modularized noise detection algorithm can be used to lessen, if not eliminate, noise from a signal, such as a cardiac signal. By modularizing each of the n-dimensional noise modules, in some examples, the algorithm can be optimized for different data types and noise sources, which can be specific to a certain medical device, a specific implanting location, a specific electrode configuration, or a specific patient disease or characteristic, for example.

Figure 8A:
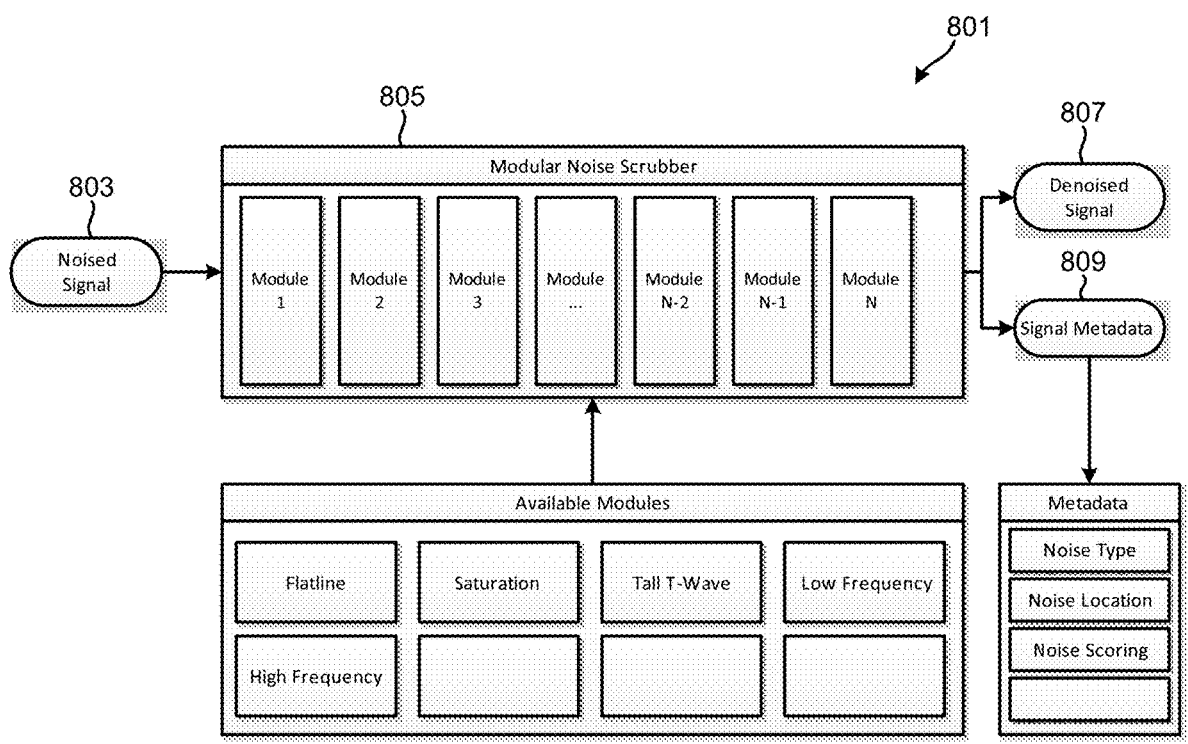
FIG. 8A illustrates an embodiment of a noise scrubber in accordance with various embodiments.

Referring to FIG. 8A, an algorithm, apparatus, system, and/or method can include one or more noise scrubber modules and outputs according to various embodiments. In some examples, a cardiac signal recorder can record three data types: scheduled trending, device detected arrhythmias, and patient triggered recordings. In some examples, data strips of these data types can be transmitted to a wireless communication device and sent to a third party cardiac monitoring center to be analyzed. False positives triggered by signal noise can be problematic, for instance, by increasing the data burden. In some examples, a noise cleaning algorithm can allow monitoring centers to scrub the incoming data and flag (reject) strips that only contain noise and no real arrhythmias, thereby decreasing the data burden.

As is shown in the embodiment illustrated in FIG. 8A, a scrubber 801 can comprise a number of different modules configured to operate on different types of noise. The representative scrubber 801 shown in FIG. 8A can include modules configured to detect a flatline signal, amplifier saturation, a tall T-wave, low frequency signal content, high frequency content, signal drift, signal amplitude attenuation, non-physiological noise, and intermittent burst noise patterns, to name a few. Other and different noise scrubbing modules are contemplated, and those shown in FIG. 8A are for non-limiting illustrative purposes. A noised ECG signal is provided at an input 803 of the scrubber 801, which is processed by a number of different scrubber modules 805. A de-noised signal is provided at an output 807 of the scrubber 801. The scrubber 801 also produces signal metadata at an output 809, according to some embodiments.

The signal metadata provided at output 809 can be a file containing information about the scrubbing modules used, the noise characteristics, and the noise location and duration as percentage of total data, for example. The metadata file can be used to improve the functionality of the scrubber 801. Perhaps more importantly, this flagging or notation provided by the metadata file can be critical in notifying the physician about what was done to the raw noisy data and the confidence he or she should have when reviewing that data. For example, very noisy data that underwent significant processing could be at risk of misrepresenting an arrhythmia due to over-filtration. Any clinical inferences made from this data may need to weigh that fact. Alternatively, if there was little truncation or filtration that was done to the raw signal, the physician could have much higher confidence in the signal. The metadata can be represented as an output in a file that can be separately accessed by the physician if they are interested in looking at that or as a symbol flag on the display screen that can indicate if the data is reliable (e.g., the color green), if moderately reliable (e.g., the color yellow), and if marginal (e.g., the color red), for example.

Figure 8B:
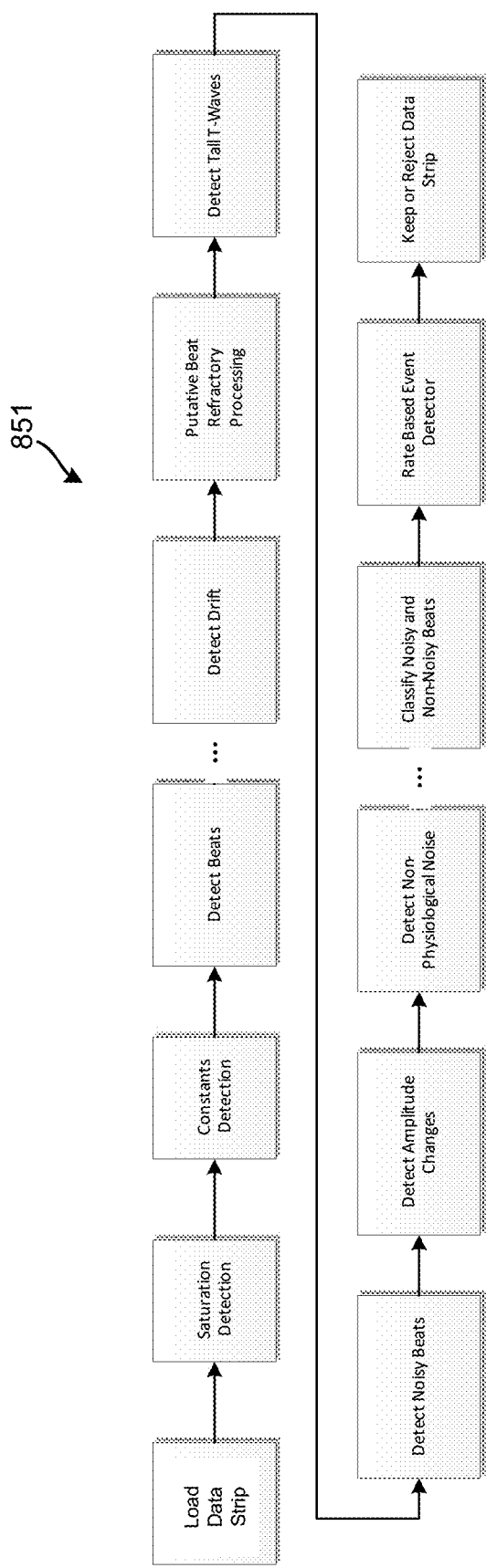
FIG. 8B illustrates an embodiment of a noise scrubber in accordance with various embodiments.

FIG. 8B shows a number of sequential processing steps 851, each step implicating a different scrubbing algorithm or module in accordance with some embodiments. A typical scrubber includes a noise scrubber function, a beat detection function, and a rate-based classification function that can be interwoven, but are largely modular and functionalized. Some or all of the processing steps 851 shown in FIG. 8B can be incorporated in a scrubber according to various embodiments. The processing steps 851 shown in FIG. 8B include data strip loading, saturation detection, constants detection, beat detection, drift detection, putative beat refractory processing, tall T-wave detection, noisy beat detection, amplitude changes detection, non-physiological noise detection, noisy and non-noisy beat detection, rate based event detection, and a keep or rejection data strip function. According to some embodiments, four processing steps or functions define the majority of the logic for the scrubber algorithm: user interface, signal processing and beat detection, scrubber core functionality, and classifying arrhythmias. Several of the processing steps shown in FIG. 8B can be considered modularized support functions for the four major processing steps or functions identified above according to some embodiments.

Figure 8C:
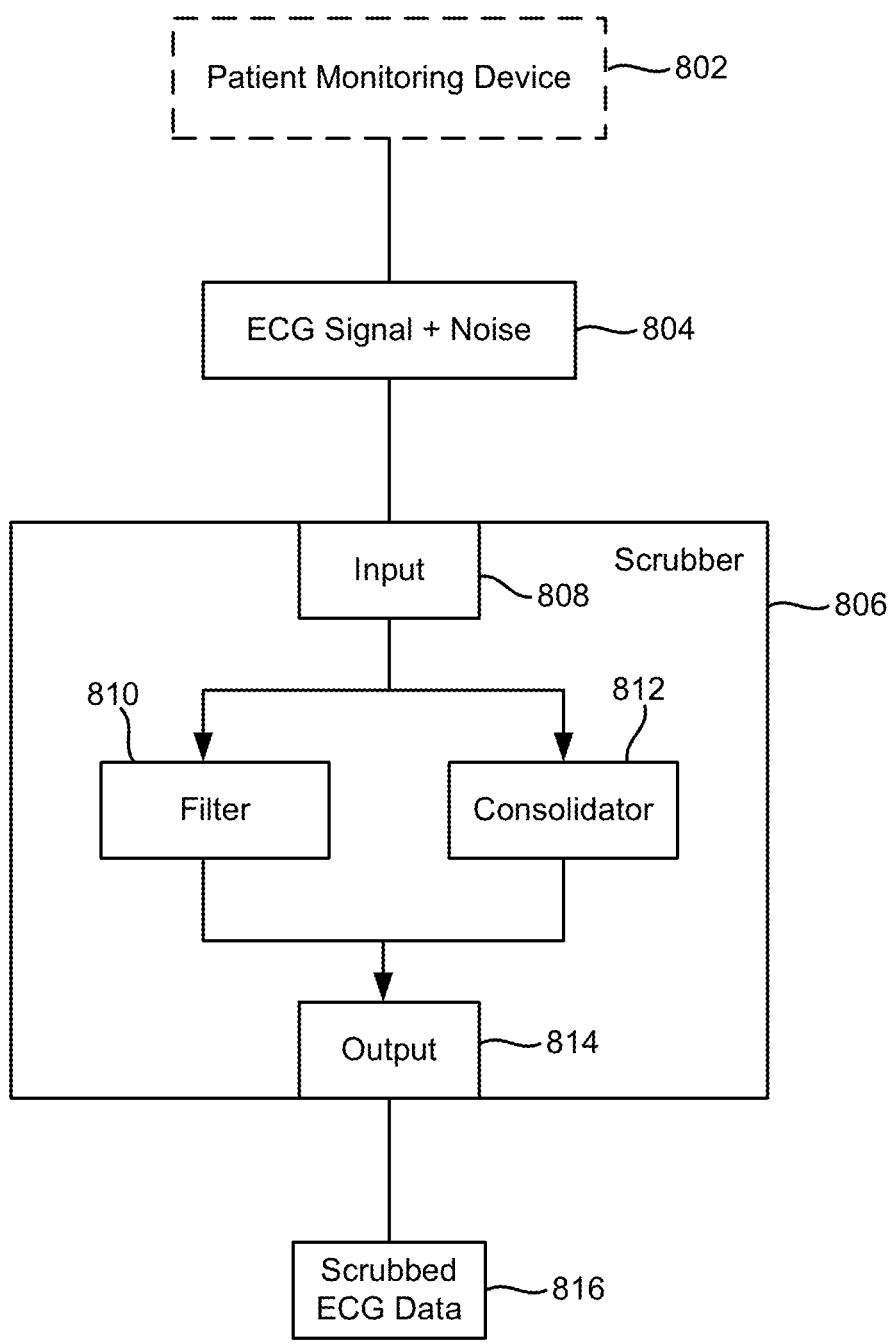
FIG. 8C illustrates an embodiment of a noise scrubber in accordance with various embodiments.

FIG. 8C illustrates an embodiment of a scrubber in accordance with various embodiments. The scrubber 806 shown in FIG. 8C receives ECG data 804 produced by a patient monitoring device 802. The scrubber 806 includes an input 808 configured to receive the ECG data 804, and includes a filter 810 and a consolidator 812. The filter 810 is configured to operate on ECG data 804 for which one or more noise segments overlap the ECG signal. The consolidator 812 is configured to operate on ECG data 804 for which one or more noise segments are non-overlapping with the ECG signal. Scrubbed ECG data 816 is provided at an output 814 of the scrubber 806.

Figure 9:
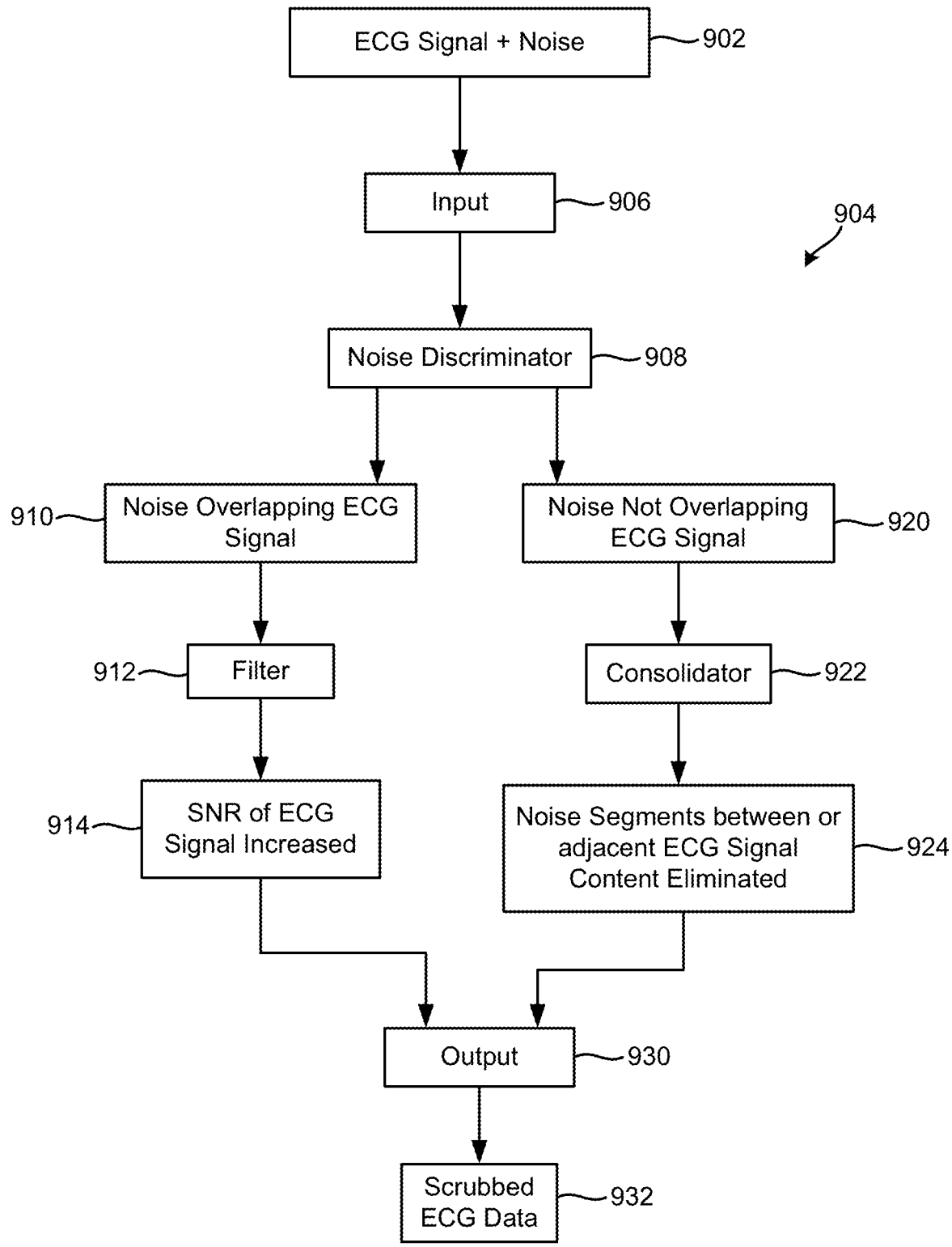
FIG. 9 illustrates various details of a noise scrubber in accordance with various embodiments.

FIG. 9 illustrates various details of a scrubber in accordance with various embodiments. The scrubber 904 shown in FIG. 9 receives ECG data 902 at an input 906, which communicates this data to a noise discriminator 908. The noise discriminator 908 is configured to analyze the ECG data 902 for the presence and location of noise within the ECG data 902. More particularly, the noise discriminator 908 is configured to distinguish between noise 910 that is overlapping with the physiologically relevant ECG signal from noise 920 that is non-overlapping with the physiologically relevant ECG signal. The ECG signal containing overlapping noise 910 is processed by a filter 912 configured to increase the signal-to-noise ratio (SNR) 914 of the ECG signal. The ECG signal containing non-overlapping noise 920 is processed by a consolidator 922. The consolidator 922 is configured to eliminate noise segments between or adjacent to the physiologically relevant ECG signal content. Scrubbed ECG data 932 produced by the filter 912 and the consolidator 922 is provided at an output 930 of the scrubber 904.

Figure 10A:
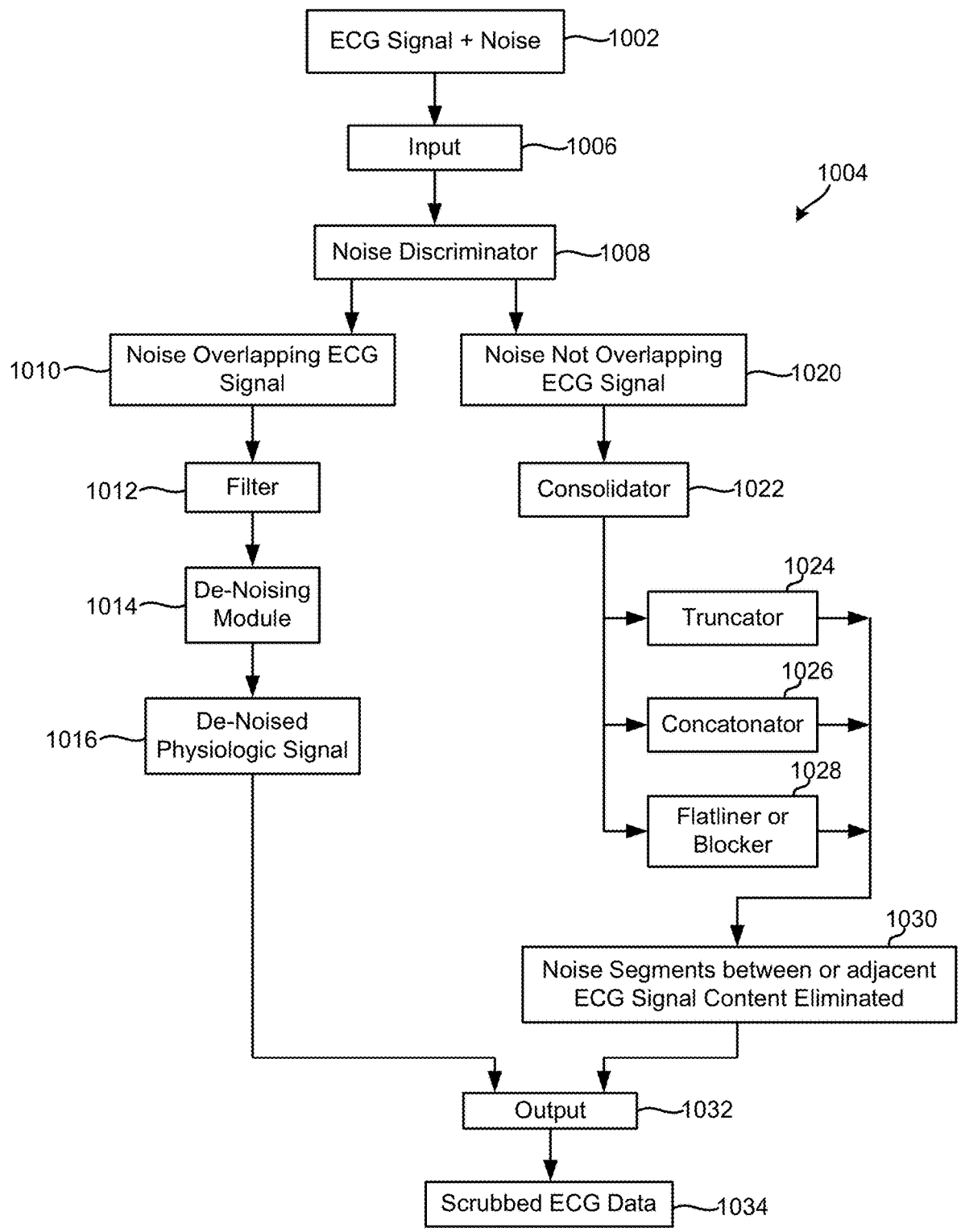
FIG. 10A illustrates various details of a noise scrubber in accordance with other embodiments.

FIG. 10A illustrates various details of a scrubber in accordance with other embodiments. The scrubber 1004 shown in FIG. 10A receives ECG data 1002 at an input 1006, which is communicated to a noise discriminator 1008. For an ECG signal with overlapping noise 1010, a de-noising module 1014 of a filter 1012 is configured to attenuate or eliminate the overlapping noise from the ECG signal to produce de-noised ECG data 1016. For example, the de-noising module 1014 can be configured to remove or attenuate one or more noise segments within the ECG data to a level that allows for classification of the overlapping physiologic signal. The de-noising module 1014 can also be configured to scale one or more noise segments within the ECG data to allow for detection of physiologically relevant signal content.

For an ECG signal with overlapping noise 1020, a consolidator 1022 can employ one of several different modules to eliminate the noise based on the location of the noise relative to the ECG signal content. The consolidator 1022 is configured to identify the location of noise within the ECG data, determine if the location is suitable for consolidation, and determine which of several available noise consolidation modules can be used to eliminate the noise based on its temporal location.

The embodiment of the consolidator 1022 shown in FIG. 10A includes three modules, a truncator 1024, a concatenator 1026, and a flatliner or blocker 1028. These three modules 1024, 1026, 1028 can operate individually or in combination on the ECG signal with overlapping noise 1022 to eliminate noise segments between or adjacent the ECG signal content 1030. Scrubbed ECG data 1034 is provided on an output 1032 of the scrubber 1004. In some embodiments, the scrubbed ECG data 1034 is evaluated to determine if the ECG data, after consolidation, comprises contiguous physiologic signal data of at least a predefined minimum duration or amount, or is sufficient to classify a physiological event. If sufficient physiologic signal data is present in the scrubbed ECG data 1034, this data can be communicated to a rhythm classifier, for example, for further processing.

The truncator 1024 is configured to operate on ECG data where the noise (e.g., noise segment) allows for truncation of the noise from the ECG signal 1104. FIGS. 11A and 11B illustrate ECG data 1102A, 1102B that can be subject to truncation by the truncator 1024. In FIG. 11A, the ECG data 1102A contains a noise segment 1106 located at the end of an ECG signal 1104. In FIG. 11B, the ECG data 1102B contains a noise segment 1108 located at the beginning of the ECG signal 1104. Because the noise segments 1106 and 1108 are located at the end and beginning of the ECG signal 1104, respectively, these noise segments 1106, 1008 can be eliminated without degrading the ECG signal 1104, since segments 1102A and 1102B are adequate to complete rhythm classification or further processing.

The concatenator 1026 is configured to operate on ECG data where the noise segments can be eliminated and viable portions of the ECG signal can be concatenated. FIG. 11C illustrates ECG data containing noise segments to be processed by the concatenator 1026. FIG. 11D illustrates the ECG data of FIG. 11C following concatenation by the concatenator 1026. In FIG. 11C, the ECG data 1112 contains two noise segments 1116 and 1118 interspersed within the ECG signal 1114. Although the noise segment 1118 can be truncated (e.g., by the truncator 1024), the noise segment 1116 cannot be truncated without losing a significant portion of the ECG signal 1114 (i.e., ECG segment 1114A or ECG segment 1114B). The concatenator 1026 is configured to eliminate the intervening noise segment 1116 and the truncator 1014 is configured to eliminate the noise segment 1118 located at the end of the ECG signal 1114. Elimination of the noise segment 1116 results in two temporally-spaced ECG signal segments 1114A and 1114B. The concatenator 1026 concatenates the two ECG signal segments 1114A and 1114B to produce a contiguous ECG signal segment 1114C shown in FIG. 11D. While the new signal segment 1114C cannot be used for temporal analysis due to concatenation, the new signal segment 1114C would contain valuable data to complete other types of analysis such as morphologic analysis, for example.

The flatliner or blocker 1028 is configured to operate on the ECG data where one or more noise segments interspersed within the ECG signal can be replaced by flatlined signal content, such as a DC signal. FIG. 11E shows ECG data 1120 that contains a noise segment 1126 located between two ECG signal segments 1124A and 1124B. The flatliner or blocker 1028 is configured to replace the noise segment 1126 with a flatlined signal segment 1128 of equal time duration, as is shown in FIG. 11F. By replacing the noise segment 1126 with the flatlined signal segment 1128, the original timing of the ECG data is preserved, allowing for temporal analyses, such as cardiac rate classification and periodicity for example.

In some embodiments, portions of the ECG data that have been modified by the filter 1012 and consolidator 1022 can be accentuated in some manner so as to be readily perceivable by a clinician. For example, de-noised segments, deleted noise segments, and flatlined segments can be highlighted using annotation, flags, and/or colorization to allow for easy review by a clinician when the ECG data is presented on a user interface (e.g., monitor of a computer). In other embodiments, the original ECG data prior to processing by the filter 1012 and consolidator 1022 can be preserved for later review by a clinician or technician, such as for evaluating the efficacy of the noise processing algorithms. Preservation of original ECG data is preferably an optionally requested feature, since it would result in an increase, rather than a decrease, in total ECG data.

Figure 10B:
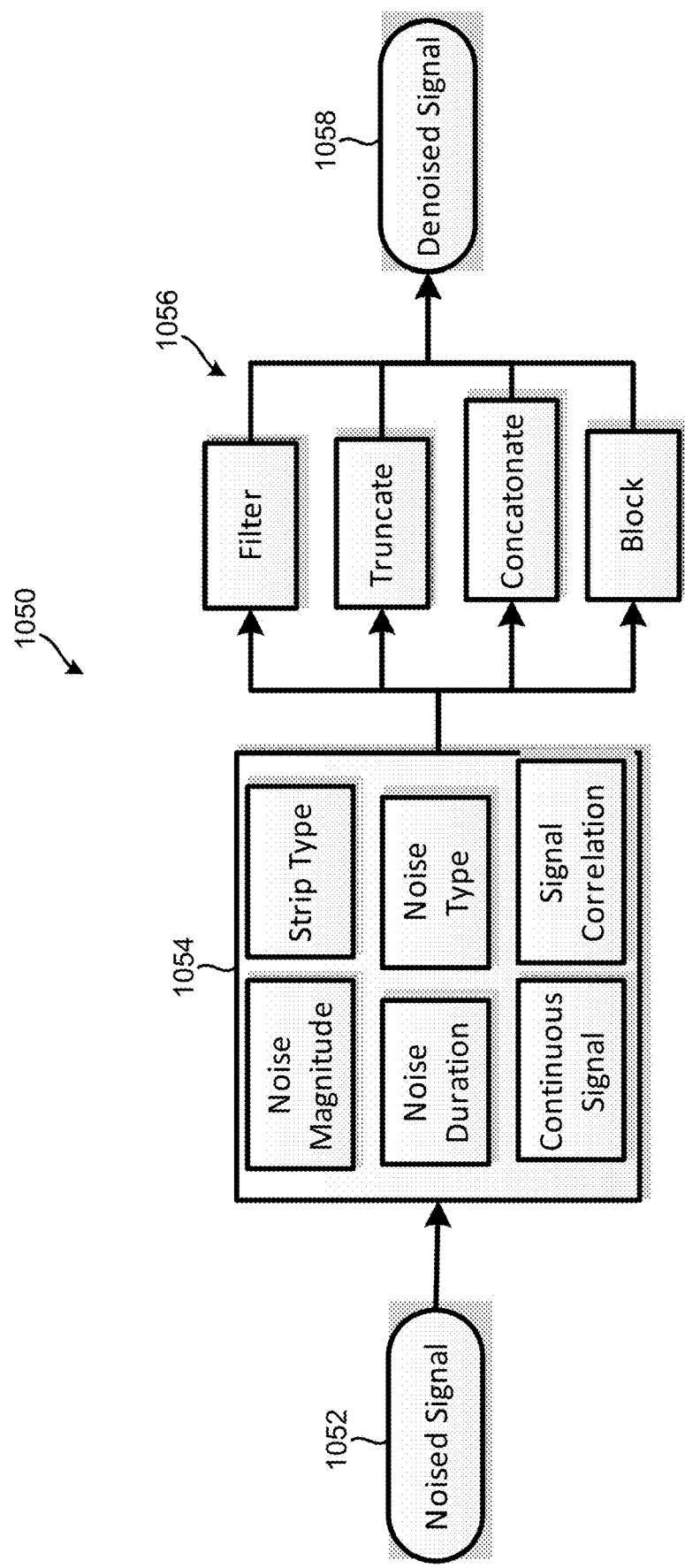
FIG. 10B illustrates de-noising signal flow through a scrubber in accordance with some embodiments.

FIG. 10B illustrates de-noising signal flow through a scrubber in accordance with other embodiments. Based on the input data, parameters, and noise detected, in some examples, algorithms implemented by the scrubber 1050 can attempt to de-noise the data using one or more of the available methods. In some examples, de-noising can be based on strip type and/or strip duration. In some examples, strip data can be used to inform how to properly clean and present data. It is noted that processing data on a strip type level (inter-strip) makes decisions for whether to keep or reject (or flag for rejection) an entire strip. This results in reduction of data burden. It is further noted that processing data within a strip (intra-strip) makes decisions on noise magnitude and duration to allow for de-noising. This results in cleaning the data to support better clinical decision making, but does not reduce data burden.

The scrubber 1050 shown in FIG. 10B receives a noised ECG signal at an input 1052, which is communicated to a noise discriminator 1054. The noise discriminator 1054 includes a number of modules each configured to process the noised ECG signal in a different manner. Representative modules of the noise discriminator 1054 shown in FIG. 10B include modules configured to detect noise magnitude, noise duration, noise type, strip type, signal continuousness, and signal correlation. Other modules 1056 of the scrubber 1050 shown in FIG. 10B, and as discussed previously, include modules configured to filter, truncate, concatenate, and block noise in the noised ECG signal. A scrubbed signal is provided at an output 1058 of the scrubber 1050.

Figure 12:
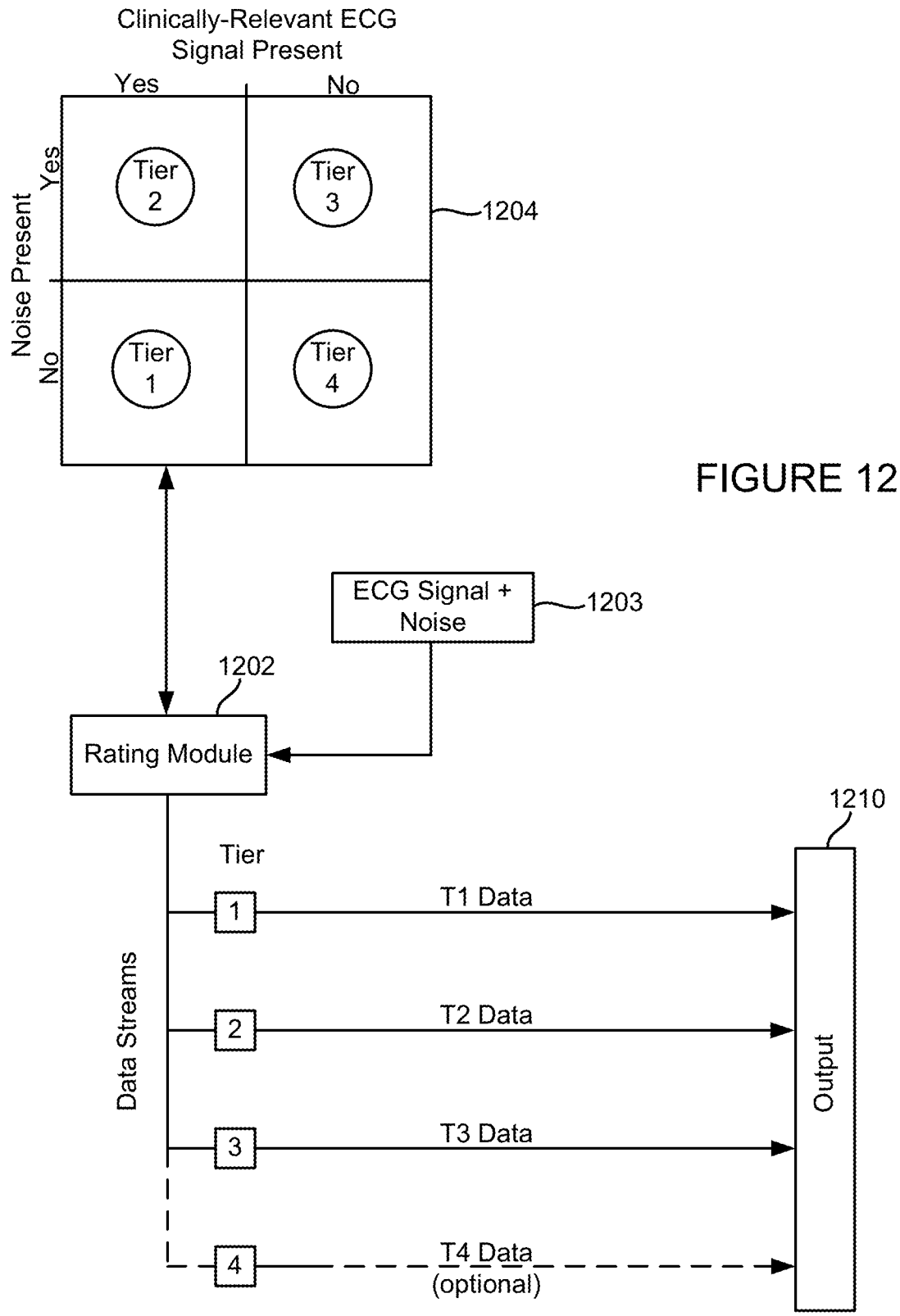
FIG. 12 illustrates various details of a rating module in accordance with various embodiments.

FIG. 12 illustrates various details of a rating module in accordance with various embodiments. The rating module 1202 is configured to receive ECG data 1203 produced from a patient monitoring device. The rating module 1202 includes or is coupled to a decision matrix 1204. The decision matrix 1204 is configured to analyze the ECG data 1203 and rate the ECG data 1203 based on the presence or absence of an ECG signal and noise in the ECG data. In the embodiment shown in FIG. 12, the decision matrix 1204 is a 2×2 matrix that is used to rate the ECG data 1203 according to four tiers. The two columns of the decision matrix 1204 indicate the presence (Yes) and absence (No) of a clinically-relevant ECG signal within the ECG data 1203, such as rate-based arrhythmias like tachycardia, or rhythm-based arrhythmias like atrial fibrillation, as examples. The two rows of the decision matrix 1204 indicate the presence (Yes) and absence (No) of noise (e.g., one or more segments of noise) within the ECG data 1203, as assessed independently or through a scrubber module as described previously.

Tier 1 (T1) data is indicated in the decision matrix 1204 as ECG data 1203 in which a clinically-relevant ECG signal is present (Yes) in the absence of noise (No). Tier 2 (T2) data is indicated in the decision matrix 1204 as ECG data 1203 in which a clinically-relevant ECG signal is present (Yes) and noise is present (Yes). Tier 3 (T3) data is indicated in the decision matrix 1204 as ECG data 1203 in which a clinically-relevant ECG signal is absent (No) and noise is present (Yes). Lastly, Tier 4 (T4) data is indicated in the decision matrix 1204 as ECG data 1203 in which an ECG signal is absent (No) and noise is also absent (No).

In some embodiments, the rating module 1202 is configured to rate the ECG data 1203 in a manner described above, and indicate the tier level of the data 1203, such as by the use of flags or annotation. In other embodiments, the rating module 1202 is configured to facilitate the production of separate data streams for each of the different tier levels. As is shown in FIG. 12, for example, four data streams (T1 Data, T2 Data, T3 Data, T4 Data) are produced, each associated with one of the tier levels T1 through T4. The disparate data streams are communicated to an output 1210 for subsequent use by other components of the system. It is noted that, in some embodiments, the T4 data stream can be discarded by the rating module 1202 and not communicated to the output 1210. In such embodiments, the T4 data stream is deemed to be a clean signal, having little or no noise, with no clinically-relevant ECG signal content that would warrant further processing. In other embodiments, the T4 data stream can be communicated to the output 1210, and be subject to evaluation by a clinician to confirm the absence of clinically-relevant ECG signal content or to evaluate the efficacy of the rating module 1202.

In some embodiments, the rating module 1202 can solely use the decision matrix 1204 to triage the ECG signal based on preset parameters, which can be static or adaptive over time. In some embodiments, the rating module 1202 can use the decision matrix 1204 in conjunction with other parametric or non-parametric input to triage the ECG signal. These additional inputs can be patient-activated, through an external mechanism, when a patient feels the onset and termination of certain symptoms, for example. In some embodiments, the external mechanism could include a patient activator peripheral device with an input capability, or a magnet swiped over the patient monitoring device, for example. In some embodiments, the additional inputs can be driven by a healthcare provider, through an external mechanism, such as when the healthcare provider wants to be notified urgently when a specific rhythm classification or noise pattern is detected, for example. The external mechanism for the healthcare provider can include web-based dedicated portal access to the patient's monitoring device or a wired/wireless mode of communication with said device, for example.

Figure 13:
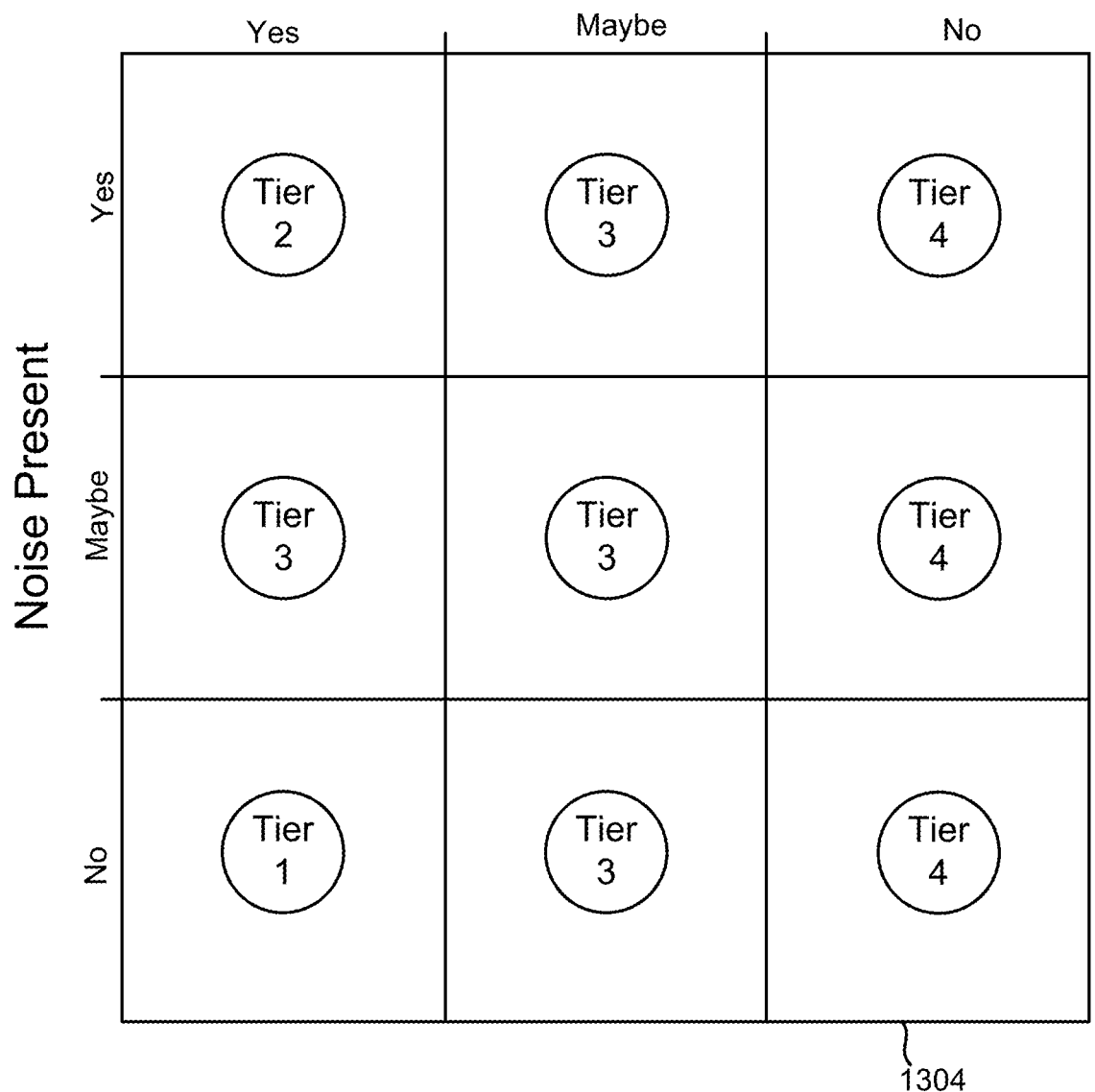
FIG. 13 illustrates a decision matrix included in or coupled to a rating module in accordance with various embodiments.

In the embodiment shown in FIG. 12, the decision matrix 1204 is a 2×2 matrix as discussed above. FIG. 13 illustrates a decision matrix 1304 that is generally representative of an n×n matrix, where n in this illustrative embodiment is equal to three. It is understood that more sophisticated decision matrices can be developed beyond 2×2 and 3×3 matrices. In the decision matrix 1304 shown in FIG. 13, three columns are used to indicate the presence (Yes), possible presence (Maybe), and absence (No) of a clinically-relevant ECG signal in the ECG data. The three rows shown in FIG. 13 are used to indicate the presence (Yes), possible presence (Maybe), and absence (No) of noise in the ECG data. Each of the combinations of columns and rows has an associated tier level ranging between T1 and T4. It is noted that the tier levels T1-T4 assigned to the boxes in the decision matrix 1204 are representative levels. It is also noted that the tier level range may include fewer or greater than four distinct levels. In a manner similar to that described in FIG. 12, the output from the decision matrix 1304 can be used to flag or annotate the ECG data according to tier level or, in other embodiments, can be used to produce disparate data streams each associated with a different tier level.

Figure 14:
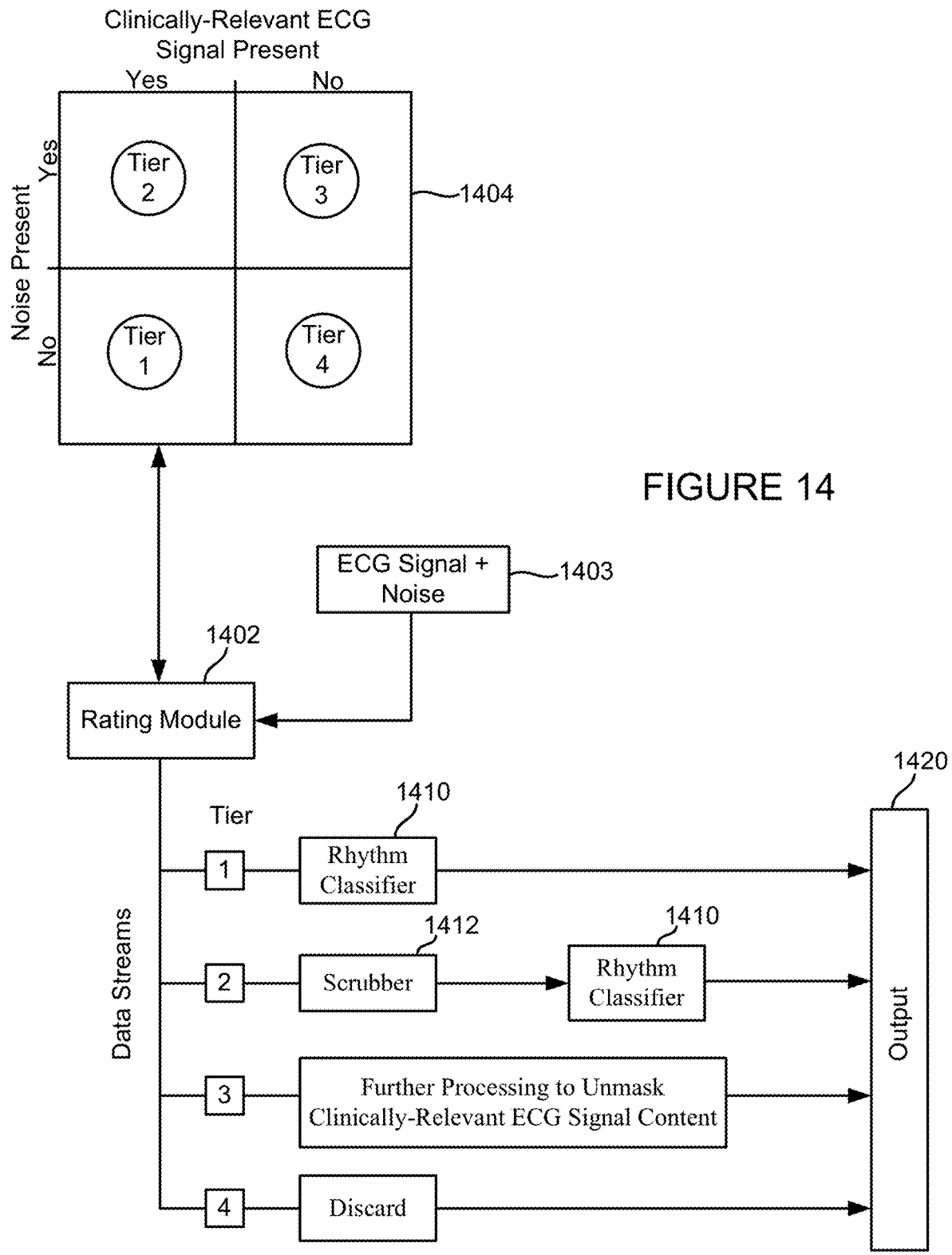
FIG. 14 is a diagram showing combined use of a rating module, a decision matrix, a noise scrubber, and a rhythm classifier in accordance with various embodiments.

FIG. 14 is a diagram showing combined use of a rating module, decision matrix, scrubber, and rhythm classifier in accordance with various embodiments. In the embodiment illustrated in FIG. 14, a rating module 1402 receives ECG signal data 1403 as an input, typically from a patient monitoring device. The rating module includes or is coupled to a decision matrix 1404, which can be a 2×2 matrix (as shown) or an n×n matrix for example. FIG. 14 shows that the tier 1 (T1) data stream is directed to the rhythm classifier 1410 without need for scrubbing. This is because the tier 1 data rated by the rating module 1402 was found to include clinically-relevant ECG signal content and has an absence of noise. As such, the rhythm classifier 1410 can operate on the tier 1 data stream without additional processing.

FIG. 14 shows that the tier 2 (T2) data stream is directed to a scrubber 1412. This is because the tier 2 data rated by the rating module 1402 was found to include clinically-relevant ECG signal content and noise. The scrubber 1412 operates on the tier 2 data stream in a manner previously described so as to increase the signal-to-noise ratio (e.g., filter) or eliminate (e.g., consolidate) the noise of the tier 2 data. The scrubbed ECG data produced at the output of the scrubber 1412 is input to the rhythm classifier 1410, which classifies cardiac rhythms in a manner previously described. The ECG data produced at the output of the rhythm classifier 1410 can include cardiac event markers and/or noise markers.

The tier 3 (T3) data shown in FIG. 14 can be subject to further processing by the rating module 1402. In some cases, ECG data that does not appear to contain clinically-relevant ECG signal content but contains noise can be subject to further processing in an attempt to recover ECG signal content that might be hidden or not readily recoverable due to the presence of noise. The tier 4 (T4) data can be discarded by the rating module 1402, since this data is not noisy to require further processing and does not contain any clinically-relevant ECG signal content.

Figure 15:
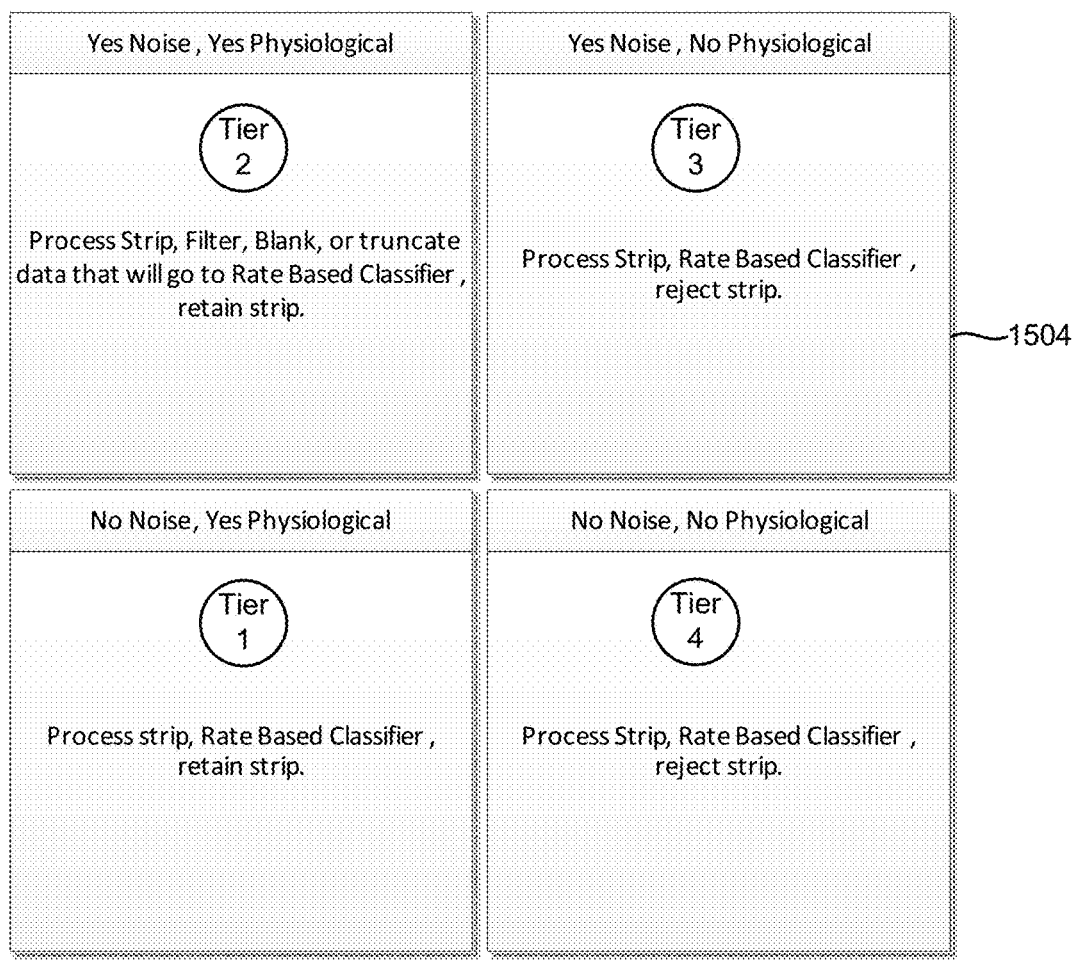
FIG. 15 illustrates a decision matrix which can be coupled to a rating module in accordance with various embodiments.

FIG. 15 illustrates a representative 2×2 decision matrix 1504 that shows additional processing performed for each of the four tiers T1-T4 of the matrix 1504. In general, logic can be implemented to complement the scrubbing process and efficiently and intelligently accept or flag (reject) data strips. Such logic is based on the outcome of two questions: 1) is there physiological signal (e.g., Tiers T1 and T2), and 2) is the signal noisy (e.g., Tiers T2 and T3). The decision matrix 1504 illustrated in FIG. 15 represents a strip flagging matrix that indicates various steps for different permutations of the answers to these two questions posed above.

In some examples, the two no-noise cases (Tiers 1 and 4) are relatively simple algorithmically. In the case of a physiological signal and no noise (Tier 1), in some examples, the strip can be classified and retained for further processing or storage. In the case of no physiological signal and no noise (Tier 4), in some examples, the classification rules will not be met and the strip will be flagged (rejected).

In some examples, the two cases with noise (Tiers 2 and 3) can include additional algorithm logic to streamline the classification process. In the case of no physiological signal and noise (Tier 3), in some examples, the signal can be scrubbed to verify the lack of physiological signal, and the strip can then be flagged (rejected) either because the classification rule is not met or because there is not enough contiguous data to allow for classification. In some examples, the final case where there is physiological signal and also noise (Tier 2) allows for strip flagging at several points in the scrubbing process.

Figure 16:
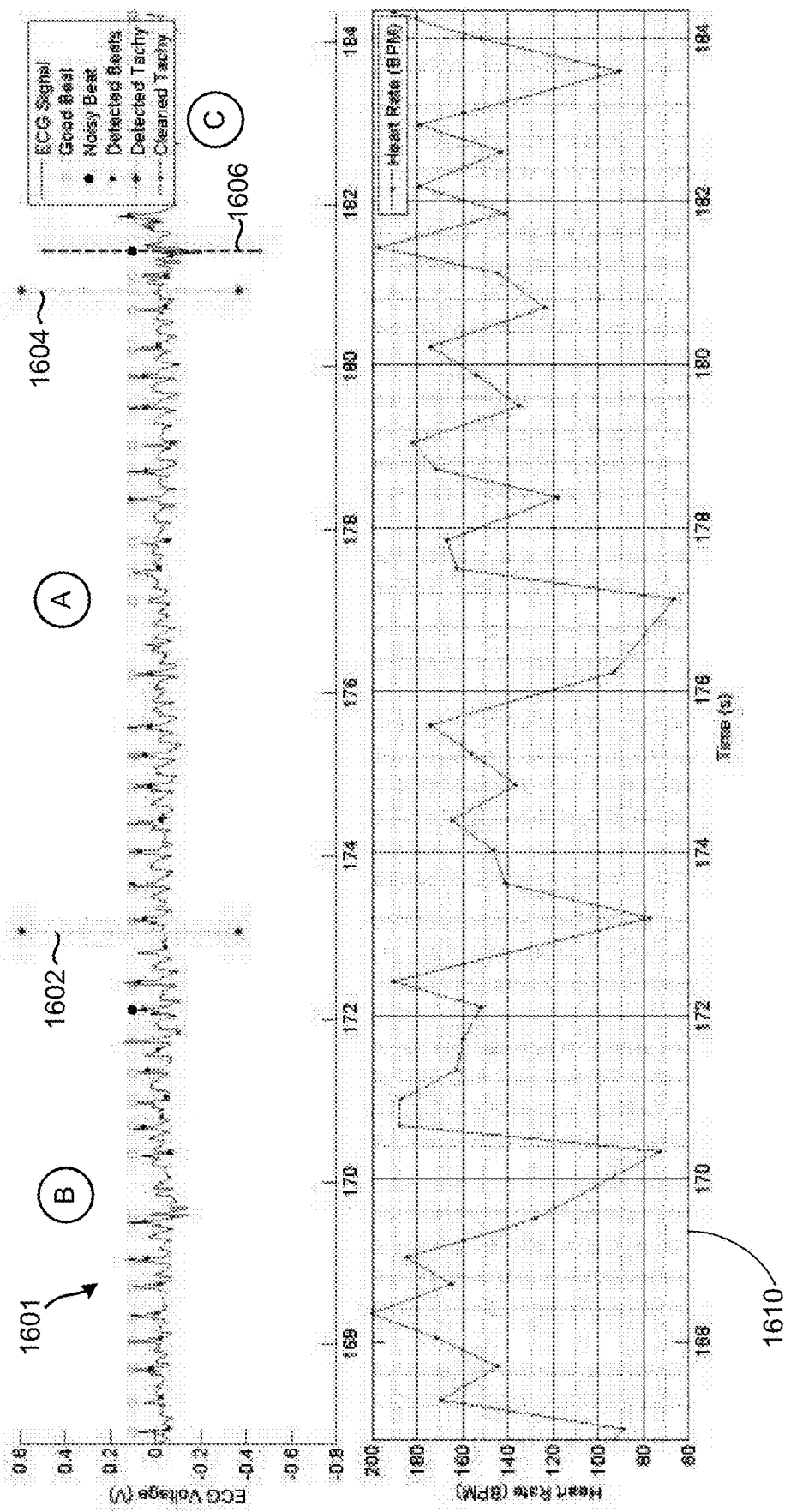
FIG. 16 is an output of a scrubber according to various embodiments.

Referring now to FIG. 16 (top panel), an output of a scrubber includes a plot of data 1601 with clean beats, noisy beats, arrhythmias, and noise graphically presented as well as the decision to flag the data according to various embodiments. In FIG. 16, open circles indicate clean (good) beats, solid circles indicate noisy beats, Xs show electrocardiogram (ECG) monitor beats, dotted vertical lines (e.g., lines 1602 and 1604) show tachycardia, dashed lines shows ECG monitor tachycardias, and dashed lines through solid circles (e.g., line 1606) show scrubber tachycardias. The ECG monitor 1610 (bottom panel) is flagging tachycardias that are noise artifacts.

The ECG monitor 1610 (bottom panel) shows the measured heart rate. The ECG monitor hardware is reporting tachycardias that are from noisy beats. In various examples, the scrubber can take into account noisy beats to lower false positives and improve true positives. In some examples, the ECG monitor 1610 can include an external device. In other examples, the ECG monitor 1610 can include an internal device. In further examples, the ECG monitor 1610 can include an implantable loop recorder (ILR). In other examples, other implantable ECG monitors can be used.

With reference again to the top panel of FIG. 16, the plot of data 1601 between dotted vertical lines 1602 and 1604 represents a zone (Zone A) of detected tachycardia. The data 1601 of Zone A represents clean data, which would be deemed acceptable by a decision matrix according to various embodiments. The portion of the data 1601 (Zone B) preceding the dotted vertical line 1602 includes one or more noisy beats and would be flagged and rejected by a decision matrix according to various embodiments. The flagged data (Zone B) of the plot of data 1601 shown in FIG. 16 would be excluded from the data 1601 output from the decision matrix.

Vertical line 1606 represents a cleaned tachycardia beat that was incorrectly detected by the ECG monitor hardware as a noisy beat. Processing of the noisy beat by a scrubber revealed clinically-relevant ECG data that was subsequently and correctly detected as a tachycardia beat. As such, the data 1601 of Zone C subsequent to the vertical line 1604 which includes the cleaned tachycardia beat 1606 can be included in the accepted data of Zone A.

CONCLUSION

The above description is intended to be illustrative, and not restrictive. For example, the above-described examples (or one or more aspects thereof) may be used in combination with each other. Other examples may be used, such as by one of ordinary skill in the art upon reviewing the above description. Also, in the above Detailed Description, various features may be grouped together to streamline the disclosure. This should not be interpreted as intending that an unclaimed disclosed feature is essential. Rather, inventive subject matter may lie in less than all features of a particular disclosed example.

What is claimed is:

1. A method for cardiac signal noise detection and disposition based on physiologic relevance, comprising:
   a) providing a user interface;
   b) providing a patient monitoring device;
   c) providing a physiologic signal processor that is in communication with the user interface and is configured to receive electrocardiogram (ECG) data detected by the patient monitoring device, at least some of the ECG data containing a cardiac signal and at least some of the ECG data containing the cardiac signal and noise;
   d) configuring the physiologic signal processor to rate the received ECG data based on the presence or absence of both the cardiac signal and the noise, wherein rating the ECG data comprises:
      i) rating and then producing, as a first tier ECG data stream, the ECG data in which the cardiac signal is present and the noise is absent;
      ii) rating and then producing, as a second tier ECG data stream, the ECG data in which the cardiac signal is present and the noise is present; and
      iii) rating and then producing, as a third tier ECG data stream, the ECG data in which the cardiac signal is absent and the noise is present; and
   e) configuring the physiologic signal processor to process each of the first, second and third data streams by:
      i) processing the first data stream with a rhythm classifier;
      ii) processing the second data stream with a scrubber followed by the rhythm classifier; and iii) processing the third data stream to unmask the cardiac signal hidden by the noise; and f) configuring the physiologic signal processor to communicate the processed first, second and third data streams to the user interface in a form that is usable by a clinician.

2. The method of claim 1, further including configuring the physiologic signal processor to rates the ECG data and then produce, as a fourth tier ECG data stream, the ECG data in which the cardiac signal is absent and the noise is absent, followed by discarding the fourth tier ECG data stream.

3. The method of claim 1, including configuring the physiological signal processor to process the second tier ECG data stream with the scrubber by:
   a) filtering one or more first noise segments of the second tier ECG data that overlap with the cardiac signal; and
   b) consolidating the second tier ECG data to eliminate one or more second noise segments, the one or more second noise segments rendering cardiac signal content of the second tier ECG data unusable for diagnostic purposes, wherein consolidating the second tier ECG data comprises one or more of:
      i) truncating the one or more second noise segments;
      ii) concatenating two or mare of the second noise segments; and
      iii) blocking or flattening the one or more second noise segments.

4. The method of claim 3, including configuring the physiological signal processor to filter the one or more first noise segments by at least one of:
   a) removing or attenuating the one or more first noise segments to a level that allows for classification of the overlapping cardiac signal by the rhythm classifier; and
   b) scaling the one or more first noise segments to allow for detection of detectable cardiac signal content.

5. The method of claim 1, including configuring the physiological signal processor to flag or annotate the ECG data based on the rating indicating the presence of noise in the ECG data.

6. The method of claim 1, including providing the user interface as a desktop computer having a monitor or a laptop computer.

7. The method of claim 1, including providing the physiologic signal processor being configured to communicate the processed first, second and third data streams to the user interface in a batch mode or real-time.

8. A medical diagnostic system, comprising:
   a) a user interface;
   b) a patient monitoring device;
   c) a physiologic signal processor that is in communication with the user interface and configured to receive physiologic signal data containing a physiologic signal and one or more artifact segments of noise from the patient monitoring device, the physiologic signal processor, comprising:
      i) an input configured to receive electrocardiogram (ECG) data detected by the patient monitoring device, at least some of the ECG data containing a cardiac signal and at least some of the ECG data containing the cardiac signal and noise; and
      ii) b) a rating module connected to the input, the rating module configured to rate the ECG data based on the presence or absence of both the cardiac signal and the noise to thereby:
         A) rate, as first tier ECG data, the ECG data in which the cardiac signal is present and the noise is absent, and then produce a first data stream for the first tier ECG data;
         B) rate, as second tier ECG data, the ECG data in which the cardiac signal is present and the noise is present, and then produce a second data stream for the second tier ECG data; and
         C) rate, as third tier ECG data, the ECG data in which the cardiac signal is absent and the noise is present, and then produce a third data stream for the third tier ECG data; and
      iii) a rhythm classifier and a scrubber connected to the rating module, wherein:
         A) the rhythm classifier is configured to process and output the first data stream to the user interface in a form that is usable to a clinician;
         B) the scrubber is configured to scrub the second data stream of noise and then send the scrubbed second data stream to the rhythm classifier, wherein the rhythm classifier is configured to process and output the scrubbed second data stream to the user interface in a form that is usable to a clinician; and
         C) the rating module is configured to process the third data stream to unmask the cardiac signal hidden by the noise and output the third data stream to the user interface in a form that is usable to a clinician.

9. The medical diagnostic system of claim 8, wherein the rating module of the physiologic signal processor is further configured to rate, as fourth tier ECG data, the ECG data in which the cardiac signal is absent and the noise is absent, and then discard the fourth tier ECG data.

10. The medical diagnostic system of claim 8, wherein the scrubber of the physiologic signal processor is configured to:
   a) filter one or more first noise segments that overlap with and render unusable for diagnostic purposes cardiac signal content of the second tier ECG data; and
   b) after filtering the one or more second tier noise segments, consolidate the second tier ECG data by one or more of:
      i) truncating the one or more second noise segments;
      ii) concatenating two or more of the second noise segments; and
      iii) blocking or flattening the one or more second noise segments.

11. The medical diagnostic system of claim 10, wherein the scrubber of the physiologic signal processor is configured to filter the one or more first noise segments by at least one of:
   a) removing or attenuating the one or more first noise segments to a level that allows for classification of the overlapping cardiac signal by the rhythm classifier; and
   b) scaling the one or more first noise segments to allow for detection of cardiac signal in the second tier ECG data by the rhythm classifier.

12. The medical diagnostic system of claim 8, wherein the rating module of the physiologic signal processor is configured to flag or annotate the ECG data based on the presence of noise in the ECG data.

13. The medical diagnostic system of claim 8, wherein the user interface is a desktop computer having a monitor or a laptop computer.

14. A method for cardiac signal noise detection and disposition based on physiologic relevance, comprising:
   a) providing a user interface;

b) providing a patient monitoring device;
c) providing a physiologic signal processor that is in communication with the user interface and configured to receive electrocardiogram (ECG) data detected by the patient monitoring device, at least some of the ECG data containing a cardiac signal and at least some of the ECG data containing the cardiac signal and noise;
d) configuring the physiologic signal processor to rate the received ECG data based on the presence or absence of both the cardiac signal and the noise, wherein rating the ECG data comprises:
   i) rating and then producing, as a first tier ECG data stream, the ECG data in which the cardiac signal is present and the noise is absent;
   ii) rating and then producing, as a second tier ECG data stream, the ECG data in which the cardiac signal is present and the noise is present; and
   iii) rating and then producing, as a third tier ECG data stream, the ECG data in which the cardiac signal is absent and the noise is present; and
e) configuring the physiologic signal processor to communicate the processed first, second and third data streams to the user interface in a form that is usable by a clinician.

15. The method of claim 14, including configuring the physiologic signal processor to process each of the first, second and third data streams by:
   a) processing the first data stream with a rhythm classifier;
   b) processing the second data stream with a scrubber followed by the rhythm classifier; and
   c) processing the third data stream to unmask the cardiac signal hidden by the noise.

16. The method of claim 14, further including configuring the physiologic signal processor to rate the ECG data and then produce, as a fourth tier ECG data stream, the ECG data in which the cardiac signal is absent and the noise is absent, followed by discarding the fourth tier ECG data stream.

17. The method of claim 14, including configuring the physiological signal processor to process the second tier ECG data stream with the scrubber by:
   a) filtering one or more first noise segments of the second tier ECG data that overlap with the cardiac signal; and
   b) consolidating the second tier ECG data to eliminate one or more second noise segments, the one or more second noise segments rendering cardiac signal content of the second tier ECG data unusable for diagnostic purposes, wherein consolidating the second tier ECG data comprises one or more of:
      i) truncating the one or more second noise segments;
      ii) concatenating two or more of the second noise segments; and
      iii) blocking or flattening the one or more second noise segments.

18. The method of claim 17, including configuring the physiological signal processor to filter the one or more first noise segments by at least one of:
   a) removing or attenuating the one or more first noise segments to a level that allows for classification of the overlapping cardiac signal by the rhythm classifier; and
   b) scaling the one or more first noise segments to allow for detection of detectable cardiac signal content.

19. The method of claim 14, including configuring the physiological signal processor to flag or annotate the ECG data based on the rating indicating the presence of noise in the ECG data.

20. The method of claim 14, including providing the user interface as a desktop computer having a monitor or a laptop computer.

* * * * *